United States Patent
Heavner et al.

(10) Patent No.: US 6,528,487 B1
(45) Date of Patent: Mar. 4, 2003

(54) PEPTIDE INHIBITORS OF INFLAMMATION MEDIATED BY SELECTINS

(75) Inventors: George A. Heavner, Flemington, NJ (US); Rodger P. McEver, Oklahoma City, OK (US); Jian-Guo Geng, Oklahoma City, OK (US)

(73) Assignees: Centocor, Inc., Malvern, PA (US); Board of Regents of the University of Oklahoma, Norman, OK (US)

( * ) Notice: Subject to any disclaimer, the term of this patent is extended or adjusted under 35 U.S.C. 154(b) by 0 days.

(21) Appl. No.: 08/135,319

(22) Filed: Oct. 12, 1993

Related U.S. Application Data

(63) Continuation of application No. 07/757,131, filed on Sep. 10, 1991, now abandoned.

(51) Int. Cl.[7] .................. A61K 38/08; A61K 38/10; A61K 38/16
(52) U.S. Cl. .............. 514/13; 514/12; 514/14; 514/15; 514/16; 514/17; 530/324; 530/325; 530/326; 530/327; 530/328; 530/329; 530/330
(58) Field of Search ............... 530/328, 327, 530/326, 324, 325, 329, 330; 514/15, 14, 13, 12, 16, 17, 21

(56) References Cited

U.S. PATENT DOCUMENTS

| | | | |
|---|---|---|---|
| 4,391,749 A | 7/1983 | Engvall et al. | 530/356 |
| 4,517,686 A | 5/1985 | Ruoslahti et al. | 623/1.49 |
| 4,578,079 A | 3/1986 | Ruoslahti et al. | 623/23.76 |

(List continued on next page.)

FOREIGN PATENT DOCUMENTS

| | | |
|---|---|---|
| WO | 90/05786 | 5/1990 |
| WO | 91/06632 | 5/1991 |
| WO | 91/07993 | 6/1991 |
| WO | 9201718 | * 2/1992 |

OTHER PUBLICATIONS

Edgington, How Sweet It Is: Selectin–Mediating Drugs, Biotechnology vol. 10, Apr., 1992.*

Beckstead, J.H, et al., "Immunohistochemical Localization of Membrane and α–Granule Proteins in Human Megakaryocytes: Application to Plastic–Embedded Bone Marrow Biopsy Specimens," *Blood*, vol. 67, No. 2 pp. 285–293, (Feb. 1986).

Berkow, R., editor, The Merck Manual of Diagnosis and Therapy, 14th Edition, pp. 649, 2404, 2405 (1982).

Bevilacqua M.P., et al., "Endotheliá Leukocyte Adhesion Molecule 1: An Inducible Receptor for Neutrophils Related to Complement Regulatory Proteins and Lectins," *Science*, vol. 243, pp. 1160–1165 (Mar. 3, 1989).

(List continued on next page.)

*Primary Examiner*—Jeffrey E. Russel
(74) *Attorney, Agent, or Firm*—Holland & Knight LLP

(57) ABSTRACT

Peptides derived from three regions of the lectin domain of GMP-140 and the related selectins, ELAM-1 and the lymphocyte homing receptor, have seen found to inhibit neutrophil adhesion to GMP-140. These and additional peptides have been synthesized, having as their core region portions of the 56–60 amino acid sequence of GMP-140, with residue 1 defined as the N-terminus of the mature protein after the cleavage of the signal peptide. Examples demonstrate the inhibition of the binding of neutrophils to GMP-140 of peptides in concentrations ranging from 5 to 1500 μmol. It has been found that alterations within the core sequence, as well as N-terminal and C-terminal flanking regions, do not result in loss of biological activity. The peptides are useful as diagnostics and, in combination with a suitable pharmaceutical carrier, for clinical applications in the modulation or inhibition of coagulation processes or inflammatory processes.

10 Claims, 1 Drawing Sheet

U.S. PATENT DOCUMENTS

| | | | |
|---|---|---|---|
| 4,589,881 A | 5/1986 | Pierschbacher et al. | 623/23.76 |
| 4,605,644 A | 8/1986 | Foker | 514/45 |
| 4,614,517 A | 9/1986 | Ruoslahti et al. | 530/330 |
| 4,661,111 A | 4/1987 | Ruoslahti et al. | 623/23.76 |
| 4,783,330 A | 11/1988 | Furie et al. | 424/1.53 |
| 4,789,734 A | 12/1988 | Pierschbacher | 530/395 |
| 4,792,525 A | 12/1988 | Ruoslahti et al. | 435/402 |
| 4,879,237 A | 11/1989 | Rudslahti et al. | 435/375 |
| 5,198,424 A * | 3/1993 | McEver | 514/13 |
| 5,266,328 A * | 11/1993 | Skubitz et al. | 424/427 |
| 6,111,065 A * | 8/2000 | Heavner et al. | 530/300 |

OTHER PUBLICATIONS

Bonfanti, R., et al., "PADGEM (GMP140) is a Component of Weibel–Palade Bodies of Human Endothelial Cells," *Blood*, vol. 73, No. 5, pp. 1109–1112 (Apr., 1989).

Bowen, B.R., et al., "Characterization of a Human Homologue of the Murine Peripheral Lymph Node Homing Receptor," *J. Cell Biol.*, vol. 109, pp. 421–427 (Jul. 1989).

Brandley, B.K., et al., "Carbohydrate Ligands of the LEC Cell Adhesion Molecules," Cell, vol. 63, pp. 861–863 (Nov. 30, 1990).

Corral, L., et al., "Requirement for Sialic Acid on Neutrophils in a GMP–140 (PADGEM) Mediated Adhesive Interaction with Activated Platelets," *Biochem. Biophys. Res. Comm.*, vol. 172, No. 3, pp. 1349–1356 (Nov. 15, 1990).

Gamble, J.R., et al., "Prevention of Activated Neutrophil Adhesion to Endothelium by Soluble Adhesion Protein GMP140," *Science*, vol. 249, pp. 414–417 (Jul. 27, 1990).

Geno, J.G., et al., "Rapid Neutrophil Adhesion to Activated Endothelium Mediated by GMP–140," *Nature*, vol. 343, No. 6260, pp. 757–760 (Feb. 22, 1990).

Goelz, S.E., et al., "ELFT: A Gene That Directs the Expression of ELAM–1 Ligand," *Cell*, vol. 63, pp. 1349–1356 (Dec. 21, 1990).

Hamburger, Steven A., et al., "GMP–140 Mediates Adhesion of Stimulated Platelets to Neutrophils," *Blood*, vol. 75, No. 3, pp. 550–554 (Feb. 1, 1990).

Hattori, R., et al., "Complement C5b–9 Stimulates von Willebrand Factor Secretion from Human Endothelium," *Abstracts of the 61st Scientific Sessions*, 0467 (Not dated).

Hattori, R., et al., "Stimulated Secretion of Endothelial von Willebrand Factor is Accompanied by Rapid Redistribution to the Cell Surface of the Intracellular Granule Membrane Protein GMP–14," *J. Biol. Chem.*, vol. 264, No. 14, pp. 7768–7771 (May 15, 1989).

Hattori, R., et al., "Complement Proteins C5b–9 Induce Secretion of High Molecular Weight Multimers of Endothelial von Willebrand Factor and Translocation of Granule Membrane Protein GMP–140 to the Cell Surface," *J. Biol. Chem.*, vol. 264, No. 15, pp. 9053–9060 (1989).

Hourcade, D., et al., "The Regulators of Complement Activation (RCA) Gene Cluster," Advances in Immunology, vol. 45, pp. 381–415 (1989).

Issenberg, William M., et al., "Cell–Cell Contact Zones of Thrombin–Induced Platelet Aggregates Lack GPIIB–IIIA and Its Ligands but Contain GMP–140," *Blood*, 70:351a, Supplement, Abstract 1261 (Nov. 1987).

Issekutz, A., et al., "Role of Neutrophils in the Deposition of Platelets during Acute Inflammation," Laboratory Invest., vol. 49, No. 6, pp. 716–724 (1983).

Johnston, G.I., et al., "Cloning of GMP–140: Chromosomal Localization, Molecular Heterogeneity and Identification of cDNAs Predicting Both Membrane Bound and Soluble Proteins," *Blood* 72:327, Supplement Abstract 1218, (Nov. 1988).

Larsen, et al., "PADGEM Protein: A Receptor that Mediates the Interaction of Activated Platelets with Neutrophils and Monocytes," *Cell*, vol. 59, pp. 305–312 (Oct. 20, 1989).

Larsen, E., et al., "PADGEM–Dependent Adhesion of Platelets to Monocytes and Neutrophils Is Mediated by a Lineage–Specific Carbohydrate, LNF III (CD15)," *Cell*, vol. 63, pp. 467–474 (Nov. 2, 1990).

Lasky, L.A., et al., "Cloning of a Lymphocyte Homing Receptor Reveals a Lectin Domain," *Cell*, vol. 56, pp. 1045–1055 (Mar. 24, 1989).

Lawrence, M.B., et al., "Leukocytes Roll on a Selectin at Physiologic Flow Rates: Distinction from and Prerequisite for Adhesion through Integrins," *Cell*, vol. 65, pp. 1–20 (May 31, 1991).

Ley, Klaus, et al., "Lectin–Like Cell Adhesion Molecule 1 Mediates Leukocyte Rolling in Mesenteric Venules In Vivo," *Blood*, vol. 77, No. 12, pp. 2553–2555 (Jun. 15, 1991).

Lowe, J.B., et al., "ELAM–1—Dependent Cell Adhesion to Vascular Endothelium Determined by a Transfected Human Fucosyltransferase cDNA," *Cell*, vol. 63, pp. 475–484 (Nov. 2, 1990).

McEver, R., et al., "A Monoclonal Antibody to a Membrane Glycoprotein Binds Only to Activated Platelets," *J. Biol. Chem.*, vol. 259, No. 15, pp. 9799–9804 (Aug. 10, 1984).

McEver, R., et al., "GMP–140, a Platelet α–Granule Membrane Protein, Is Also Synthesized by Vascular Endothelial Cells and Is Localized in Weibel–Palade Bodies," *J. Clin. Invest.*, vol. 84, pp. 92–99 (Jul. 1989).

McEver, et al., "GMP–140: A Receptor for Neutrophils and Monocytes on Activated Platelets and Endothelium," *Journal of Cellular Biochemistry* vol. 45, pp. 1–6 (1990).

McEver, et al., "The Platelet α–Granule Membrane Protein GMP–140 is Also Synthesized by Human Vascular Endothelial Cells and is Present in Blood VEssels of Diverse Tissues," *Blood* 70(5) Suppl. 1:355a, Abstract No. 1274 (1987).

McEver, et al., "Properties of GMP–140, an Inducible Granule Membrane Protein of Platelets and Endothelium," *Blood Cells*, vol. 16, pp. 73–83 (1990).

McEver, R., "Selectins: Novel Receptors that Mediate Leukocyte Adhesion During Inflammation," Thrombosis and Haemostasis Review Article, F.K. Schattauer Verlagsgesellschaft mbH (Stuttgart) 65 (3) 223–228 (1991).

Mileski, W.J., et al., "Inhibition of CD17–Dependent Neutrophil Adherence Reduces Organ Injury after Hemorrhagic Shock in Primates," *Surgery*, vol. 108, No. 2, pp. 206–212 (Aug. 1990).

Mileski, W.J., et al., "Transient Inhibition of Neutrophil Adherence with the Anti–CD18 Monoclonal Antibody 60.3 Does Not Increase Mortality Rates in Abdominal Sepsis," *Surgery*, vol. 109, No. 4, pp. 497–501 (Apr. 1991).

Moore, et al., "GMP–140 Binds to a Glycoprotein Receptor on Human Neutrophils Evidence for a Lectin–like Interaction," *J. Cell Biol.*, vol. 112, pp. 491–499 (1991).

Siegelman, M.H., et al., "Human Homologue of Mouse Lymph Node Homing Receptor: Evolutionary Conservation at Tandem Cell Interaction Domains," *Proc. Natl. Aca. Sci.*, vol. 86, pp. 5562–5566 (Jul. 1989).

Siegelman, M.H., et al., "Mouse Lymph Node Homing Receptor cDNA Clone Encodes a Glycoprotein Revealing Tandem Interaction Domains," *Science*, vol. 243, pp. 1165–1172 (Mar. 3, 1989).

Skinner, Michael P., et al., "Characterization of Human Platelet GMP–140 as a Heparin–Binding Protein," Biochem. Biophys. *Res. Comm.*, vol. 164, pp. 1373–1379 (1989).

Skinner, Michael P., et al., "GMP–140 Binding to Neutrophils is Inhibited by Sulfated Glycans," Journal of Biological Chemistry, vol. 266, No. 9, pp. 5371–5374 (Mar. 25, 1991).

Springer, T.A., et al., "Sticky Sugars for Selectins," *Nature*, vol. 349, pp. 196–197 (Jan. 17, 1991).

Stenberg, P., et al., "A Platelet Alpha–Granule Membrane Protein (GMP–140) is Expressed on the Plasma Membrane after Activation," *J. Cell Biol.*, vol. 101, pp. 880–886 (1985).

Tedder, T., et al., "Isolation and Chromosomal Localization of cDNAs Encoding a Novel Human Lymphocyte Cell Surface Molecule, LAM–1," *J. Exp. Med.* vol. 170, pp. 123–133 (Jul. 1989).

Tiemeyer, M., et al., "Carbohydrate Ligands for Endothelial–Leukocyte Adhesion Molecule 1," *Proc. Natl. Acad. Sci.*, vol. 88, pp. 1138–1142 (Feb. 1991).

Tuomanen, E.I., et al., "Reduction of Inflammation, Tissue Damage, and Mortality in Bacterial Meningitis in Rabbits Treated with Monoclonal Antibodies Against Adhesion––Promoting Receptors of Leukocytes," *J. Exp. Med.*, vol. 170, pp. 959–969 (Sep. 1989).

Vedder, N.B., et al., "A Monoclonal Antibody to the Adherence–Promoting Leukocyte Glycoprotein, CD18, Reduces Organ Injury and Improves Survival from Hemorrhagic Shock and Resuscitation in Rabbits," *J. Clin. Invest.*, vol. 81, pp. 939–944 (Mar. 1988).

von Andrian, Ulrich H., et al., "Two Step Model of Leukocyte–Endothelial Cell Interaction in Inflammation: Distinct Roles for LECAM–1 and the Leukocyte β2 Integrins In Vivo," *Proc. Natl. Acad. Sci.*, vol. 88, No. 17 pp. 7538–7542 (Sep. 1, 1991).

Walz, G., et al., "Recognition by ELAM–1 of the Sialyl–Le$^x$ Determinant on Myeloid and Tumor Cells," Science, vol. 250, pp. 1132–1135 (Nov. 23, 1990).

Watson, Mark L., et al., "Genomic Organization of the Selectin Family of Leukocyte Adhesion Molecules on Human and Mouse Chromosome 1," *J. Exp. Med.*, vol. 172, pp. 263–271 (Jul. 1990).

Watson, Susan R., et al., "Neutrophil Influx into an Inflammatory Site Inhibited by a Soluble Homing Receptor–IgG Chimaera," *Nature*, vol. 349, pp. 164–167 (Jan. 10, 1991).

Zimmerman, Guy A., et al., "Thrombin Stimulates Neutrophil Adherence by an Endothelial Cell–Dependent Mechanism: Characterization of the Response and Relationship to Platelet–Activating Factor Synthesis," *Annals New York Academy of Sciences*, vol. 485, pp. 349–368 (1986).

Johnston, G.I., et al., "Cloning of GMP–140, a Granule Membrane Protein of Platelets and Endothelium: Sequence Similarity to Proteins Involved in Cell Adhesion and Inflammation," *Cell*, vol. 56, pp. 1033–1044 (Mar. 24, 1989).

Johnston, G.I., et al., "Structural and Biosynthetic Studies of the Granule Membrane Protein, GMP–140, from Human Platelets and Endothelial Cells," *J. Biol. Chem.* vol. 264, No. 3, pp. 1816–1823 (1989).

Johnston, G.I., et al., "Structure and Biosynthesis of the Platelet α–Granule Membrane Protein, GMP–140," Blood, 70(5), Suppl. 1:352a, Abstract 1264, (1987).

Johnston, G.I., et al., "Structure of the Human Gene Encoding Granule Membrane Protein–140, a Member of the Selectin Family of Adhesion Receptors for Leukocytes," *J. Biol. Chem.* vol. 265, No. 34, pp. 21381–21385 (Dec. 5, 1990).

Jungi, et al., "Platelet–Leukocyte Interaction: Selective Binding of Thrombin–Stimulated Platelets to Human Monocytes, Polymorphonuclear Leukocytes, and Related Cell Lines," *Blood* 67:629–636 (1986).

Müller–Eberhard, H., "Molecular Organization and Function of the Complement System," *Ann. Rev. Biochem.* vol. 57, pp. 321–347 (1988).

Ord, D.C., et al., "Structure of the Gene Encoding the Human Leukocyte Adhesion Molecule–1)TQ1, Leu–8) of Lymphocytes and Neutrophils," *The Journal of Biological Chemistry*, vol. 265, No. 14, pp. 7760–7767 (1990).

Patel, K.D., et al., "Oxygen Radicals Induce Human Endothelial Cells to Express GMP–140 and Bind Neutrophils," *J. Cell. Biol.*, vol. 112, No. 4, pp. 749–759 (Feb. 1991).

Phillips, M.L., et al., "ELAM–1 Mediates Cell Adhesion by Recognition of a Carbohydrate Ligand, Sialyl–Le$^x$," *Science*, vol. 250, pp. 1130–1131 (Nov. 23, 1990).

Rosen, S.D., "'The LEC–CAMs' An Emerging Family of Cell Adhesion Receptors Based upon Carbohydrate Recognition," *Am. J. Respir. Cell Mol. Biol.*, vol. 3, pp. 397–402 (1990).

Simpson, P.J., et al., "Reduction of Experimental Canine Myocardial Reperfusion Injury by a Monoclonal Antibody (Anti–Mo1, Anti–CD11b) That Inhibits Leukocyte Adhesion," *J. Clin. Invest.*, vol. 81, pp. 624–629 (Feb. 1988).

* cited by examiner

SEQUENCE LISTING

<160> NUMBER OF SEQ ID NOS: 36

<210> SEQ ID NO 1
<211> LENGTH: 10
<212> TYPE: PRT
<213> ORGANISM: artificial sequence
<220> FEATURE:
<223> OTHER INFORMATION: Synthetic inhibitory peptide

<400> SEQUENCE: 1

Arg Lys Asn Asn Lys Thr Trp Thr Trp Val
1               5                   10

<210> SEQ ID NO 2
<211> LENGTH: 10
<212> TYPE: PRT
<213> ORGANISM: artificial sequence
<220> FEATURE:
<223> OTHER INFORMATION: Synthetic inhibitory peptide

<400> SEQUENCE: 2

Arg Lys Val Asn Asn Val Trp Val Trp Val
1               5                   10

<210> SEQ ID NO 3

```
<211> LENGTH: 10
<212> TYPE: PRT
<213> ORGANISM: artificial sequence
<220> FEATURE:
<223> OTHER INFORMATION: Synthetic inhibitory peptide
<221> NAME/KEY: MISC_FEATURE
<222> LOCATION: (10)..(10)
<223> OTHER INFORMATION: No NH2

<400> SEQUENCE: 3

Arg Lys Val Asn Asn Val Trp Val Trp Val
1               5                   10

<210> SEQ ID NO 4
<211> LENGTH: 10
<212> TYPE: PRT
<213> ORGANISM: artificial sequence
<220> FEATURE:
<223> OTHER INFORMATION: Synthetic inhibitory peptide

<400> SEQUENCE: 4

Arg Lys Ile Gly Gly Ile Trp Thr Trp Val
1               5                   10

<210> SEQ ID NO 5
<211> LENGTH: 10
<212> TYPE: PRT
<213> ORGANISM: artificial sequence
<220> FEATURE:
<223> OTHER INFORMATION: Synthetic inhibitory peptide
<221> NAME/KEY: MISC_FEATURE
<222> LOCATION: (1)..(1)
<223> OTHER INFORMATION: D-arginine

<400> SEQUENCE: 5

Arg Lys Ile Gly Gly Ile Trp Thr Trp Val
1               5                   10

<210> SEQ ID NO 6
<211> LENGTH: 10
<212> TYPE: PRT
<213> ORGANISM: artificial sequence
<220> FEATURE:
<223> OTHER INFORMATION: Synthetic inhibitory peptide
<221> NAME/KEY: MISC_FEATURE
<222> LOCATION: (2)..(2)
<223> OTHER INFORMATION: D-lysine

<400> SEQUENCE: 6

Arg Lys Ile Gly Gly Ile Trp Thr Trp Val
1               5                   10

<210> SEQ ID NO 7
<211> LENGTH: 11
<212> TYPE: PRT
<213> ORGANISM: artificial sequence
<220> FEATURE:
<223> OTHER INFORMATION: Synthetic inhibitory peptide

<400> SEQUENCE: 7

Cys Arg Lys Asn Asn Lys Thr Trp Thr Trp Val
1               5                   10

<210> SEQ ID NO 8
<211> LENGTH: 10
<212> TYPE: PRT
<213> ORGANISM: artificial sequence
<220> FEATURE:
<223> OTHER INFORMATION: Synthetic inhibitory peptide
```

```
<400> SEQUENCE: 8

Tyr Lys Asn Asn Lys Thr Trp Thr Trp Val
1               5                   10

<210> SEQ ID NO 9
<211> LENGTH: 10
<212> TYPE: PRT
<213> ORGANISM: artificial sequence
<220> FEATURE:
<223> OTHER INFORMATION: Synthetic inhibitory peptide

<400> SEQUENCE: 9

Arg Glu Asn Asn Lys Thr Trp Thr Trp Val
1               5                   10

<210> SEQ ID NO 10
<211> LENGTH: 10
<212> TYPE: PRT
<213> ORGANISM: artificial sequence
<220> FEATURE:
<223> OTHER INFORMATION: Synthetic inhibitory peptide

<400> SEQUENCE: 10

Arg Lys Asn Asn Gly Thr Trp Thr Trp Val
1               5                   10

<210> SEQ ID NO 11
<211> LENGTH: 5
<212> TYPE: PRT
<213> ORGANISM: artificial sequence
<220> FEATURE:
<223> OTHER INFORMATION: Synthetic inhibitory peptide
<221> NAME/KEY: MISC_FEATURE
<222> LOCATION: (1)..(1)
<223> OTHER INFORMATION: Fluorenylmethoxycarbonyl bound at position 1

<400> SEQUENCE: 11

Asn Asn Lys Thr Trp
1               5

<210> SEQ ID NO 12
<211> LENGTH: 10
<212> TYPE: PRT
<213> ORGANISM: artificial sequence
<220> FEATURE:
<223> OTHER INFORMATION: Synthetic inhibitory peptide

<400> SEQUENCE: 12

Lys Trp Lys Trp Asn Arg Thr Asn Val Thr
1               5                   10

<210> SEQ ID NO 13
<211> LENGTH: 7
<212> TYPE: PRT
<213> ORGANISM: artificial sequence
<220> FEATURE:
<223> OTHER INFORMATION: Synthetic inhibitory peptide

<400> SEQUENCE: 13

Arg Lys Asn Asn Lys Thr Trp
1               5

<210> SEQ ID NO 14
<211> LENGTH: 14
<212> TYPE: PRT
<213> ORGANISM: artificial sequence
```

```
<220> FEATURE:
<223> OTHER INFORMATION: Synthetic inhibitory peptide

<400> SEQUENCE: 14

Cys Ile Gly Ile Arg Lys Asn Asn Lys Thr Trp Thr Trp Val
1               5                   10

<210> SEQ ID NO 15
<211> LENGTH: 20
<212> TYPE: PRT
<213> ORGANISM: artificial sequence
<220> FEATURE:
<223> OTHER INFORMATION: Synthetic inhibitory peptide

<400> SEQUENCE: 15

Arg Lys Asn Asn Lys Thr Trp Thr Trp Val Gly Thr Lys Lys Ala Leu
1               5                   10                  15

Thr Asn Glu Cys
            20

<210> SEQ ID NO 16
<211> LENGTH: 6
<212> TYPE: PRT
<213> ORGANISM: artificial sequence
<220> FEATURE:
<223> OTHER INFORMATION: Synthetic inhibitory peptide

<400> SEQUENCE: 16

Lys Asn Asn Lys Thr Trp
1               5

<210> SEQ ID NO 17
<211> LENGTH: 5
<212> TYPE: PRT
<213> ORGANISM: artificial sequence
<220> FEATURE:
<223> OTHER INFORMATION: Synthetic inhibitory peptide
<221> NAME/KEY: MOD_RES
<222> LOCATION: (1)..(1)
<223> OTHER INFORMATION: ACETYLATION

<400> SEQUENCE: 17

Asn Asn Lys Thr Trp
1               5

<210> SEQ ID NO 18
<211> LENGTH: 10
<212> TYPE: PRT
<213> ORGANISM: artificial sequence
<220> FEATURE:
<223> OTHER INFORMATION: Synthetic inhibitory peptide
<221> NAME/KEY: MISC_FEATURE
<222> LOCATION: (10)..(10)
<223> OTHER INFORMATION: No NH2

<400> SEQUENCE: 18

Arg Lys Asn Asn Lys Thr Trp Thr Trp Val
1               5                   10

<210> SEQ ID NO 19
<211> LENGTH: 10
<212> TYPE: PRT
<213> ORGANISM: artificial sequence
<220> FEATURE:
<223> OTHER INFORMATION: Synthetic inhibitory peptide
<221> NAME/KEY: MISC_FEATURE
<222> LOCATION: (10)..(10)
<223> OTHER INFORMATION: No NH2
```

```
<400> SEQUENCE: 19

Arg Lys Ile Gly Gly Ile Trp Thr Trp Val
1               5                   10

<210> SEQ ID NO 20
<211> LENGTH: 7
<212> TYPE: PRT
<213> ORGANISM: artificial sequence
<220> FEATURE:
<223> OTHER INFORMATION: Synthetic inhibitory peptide

<400> SEQUENCE: 20

Arg Lys Ile Gly Gly Ile Trp
1               5

<210> SEQ ID NO 21
<211> LENGTH: 7
<212> TYPE: PRT
<213> ORGANISM: artificial sequence
<220> FEATURE:
<223> OTHER INFORMATION: Synthetic inhibitory peptide

<400> SEQUENCE: 21

Arg Lys Val Asn Asn Val Trp
1               5

<210> SEQ ID NO 22
<211> LENGTH: 10
<212> TYPE: PRT
<213> ORGANISM: artificial sequence
<220> FEATURE:
<223> OTHER INFORMATION: Synthetic inhibitory peptide
<221> NAME/KEY: MOD_RES
<222> LOCATION: (1)..(1)
<223> OTHER INFORMATION: ACETYLATION

<400> SEQUENCE: 22

Arg Lys Asn Asn Lys Thr Trp Thr Trp Val
1               5                   10

<210> SEQ ID NO 23
<211> LENGTH: 10
<212> TYPE: PRT
<213> ORGANISM: artificial sequence
<220> FEATURE:
<223> OTHER INFORMATION: Synthetic inhibitory peptide

<400> SEQUENCE: 23

Arg Lys Asn Asn Lys Thr Trp Thr Trp Glu
1               5                   10

<210> SEQ ID NO 24
<211> LENGTH: 17
<212> TYPE: PRT
<213> ORGANISM: artificial sequence
<220> FEATURE:
<223> OTHER INFORMATION: Synthetic inhibitory peptide

<400> SEQUENCE: 24

Arg Lys Asn Asn Lys Thr Trp Thr Trp Val Gly Thr Lys Lys Ala Leu
1               5                   10                  15

Cys

<210> SEQ ID NO 25
<211> LENGTH: 9
```

```
<212> TYPE: PRT
<213> ORGANISM: artificial sequence
<220> FEATURE:
<223> OTHER INFORMATION: Synthetic inhibitory peptide

<400> SEQUENCE: 25

Arg Lys Asn Asn Lys Thr Trp Thr Trp
1               5

<210> SEQ ID NO 26
<211> LENGTH: 8
<212> TYPE: PRT
<213> ORGANISM: artificial sequence
<220> FEATURE:
<223> OTHER INFORMATION: Synthetic inhibitory peptide

<400> SEQUENCE: 26

Arg Lys Asn Asn Lys Thr Trp Thr
1               5

<210> SEQ ID NO 27
<211> LENGTH: 4
<212> TYPE: PRT
<213> ORGANISM: artificial sequence
<220> FEATURE:
<223> OTHER INFORMATION: region of artificial inhibitory peptide

<400> SEQUENCE: 27

Gly Ile Arg Lys
1

<210> SEQ ID NO 28
<211> LENGTH: 5
<212> TYPE: PRT
<213> ORGANISM: artificial sequence
<220> FEATURE:
<223> OTHER INFORMATION: region of artificial inhibitory peptide

<400> SEQUENCE: 28

Ile Gly Ile Arg Lys
1               5

<210> SEQ ID NO 29
<211> LENGTH: 6
<212> TYPE: PRT
<213> ORGANISM: artificial sequence
<220> FEATURE:
<223> OTHER INFORMATION: region of artificial inhibitory peptide

<400> SEQUENCE: 29

Cys Ile Gly Ile Arg Lys
1               5

<210> SEQ ID NO 30
<211> LENGTH: 6
<212> TYPE: PRT
<213> ORGANISM: artificial sequence
<220> FEATURE:
<223> OTHER INFORMATION: region of artificial inhibitory peptide

<400> SEQUENCE: 30

Thr Trp Val Gly Thr Lys
1               5

<210> SEQ ID NO 31
<211> LENGTH: 6
<212> TYPE: PRT
```

```
<213> ORGANISM: artificial sequence
<220> FEATURE:
<223> OTHER INFORMATION: region of artificial inhibitory peptide

<400> SEQUENCE: 31

Thr Trp Val Gly Thr Asn
1               5

<210> SEQ ID NO 32
<211> LENGTH: 6
<212> TYPE: PRT
<213> ORGANISM: artificial sequence
<220> FEATURE:
<223> OTHER INFORMATION: region of artificial inhibitory peptide

<400> SEQUENCE: 32

Thr Trp Val Gly Thr Gln
1               5

<210> SEQ ID NO 33
<211> LENGTH: 6
<212> TYPE: PRT
<213> ORGANISM: artificial sequence
<220> FEATURE:
<223> OTHER INFORMATION: region of artificial inhibitory peptide

<400> SEQUENCE: 33

Val Trp Val Gly Thr Gln
1               5

<210> SEQ ID NO 34
<211> LENGTH: 6
<212> TYPE: PRT
<213> ORGANISM: artificial sequence
<220> FEATURE:
<223> OTHER INFORMATION: region of artificial inhibitory peptide

<400> SEQUENCE: 34

Val Trp Val Gly Thr Lys
1               5

<210> SEQ ID NO 35
<211> LENGTH: 6
<212> TYPE: PRT
<213> ORGANISM: artificial sequence
<220> FEATURE:
<223> OTHER INFORMATION: region of artificial inhibitory peptide

<400> SEQUENCE: 35

Val Trp Val Gly Thr Asn
1               5

<210> SEQ ID NO 36
<211> LENGTH: 13
<212> TYPE: PRT
<213> ORGANISM: artificial sequence
<220> FEATURE:
<223> OTHER INFORMATION: region of artificial inhibitory peptide

<400> SEQUENCE: 36

Thr Trp Val Gly Thr Lys Lys Ala Leu Thr Asn Glu Cys
1               5                   10
```

PEPTIDE INHIBITORS OF INFLAMMATION MEDIATED BY SELECTINS

CROSS REFERENCE TO RELATED APPLICATIONS

This is a continuation of co-pending application U.S. Ser. No. 07/757,131 filed on Sep. 10, 1991, by George A. Heavner, Rodger P. McEver, and Jian-Guo Geng entitled "Peptide Inhibitors of Inflamation Mediated by Selectins", now abandoned.

BACKGROUND OF THE INVENTION

This invention is generally in the field of methods of the treatment and prevention of inflammatory responses using peptides derived from selectins including GMP-140, ELAM-1, and lymphocyte-homing receptor.

The adherence of platelets and leukocytes to vascular surfaces is a critical component of the inflammatory response, and is part of a complex series of reactions involving the simultaneous and interrelated activation of the complement, coagulation, and immune systems.

The complement proteins collectively play a leading role in the immune system, both in the identification and in the removal of foreign substances and immune complexes, as reviewed by Muller-Eberhard, H. J., *Ann. Rev. Biochem.* 57:321–347 (1988). Central to the complement system are the C3 and C4 proteins, which when activated covalently attach to nearby targets, marking them for clearance. In order to help control this process, a remarkable family of soluble and membrane-bound regulatory proteins has evolved, each of which interacts with activated C3 and/or C4 derivatives. The coagulation and inflammatory pathways are regulated in a coordinate fashion in response to tissue damage. For example, in addition to becoming adhesive for leukocytes, activated endothelial cells express tissue factor on the cell surface and decrease their surface expression of thrombomodulin, leading to a net facilitation of coagulation reactions on the cell surface. In some cases, a single receptor can be involved in both inflammatory and coagulation processes.

Leukocyte adherence to vascular endothelium is a key initial step in migration of leukocytes to tissues in response to microbial invasion. Although a class of inducible leukocyte receptors, the CD11–CD18 molecules, are thought to have some role in adherence to endothelium, mechanisms of equal or even greater importance for leukocyte adherence appear to be due to inducible changes in the endothelium itself.

Activated platelets have also been shown to interact with both neutrophils and monocytes in vitro. The interaction of platelets with monocytes may be mediated in part by the binding of thrombospondin to platelets and monocytes, although other mechanisms have not been excluded. The mechanisms for the binding of neutrophils to activated platelets are not well understood, except that it is known that divalent cations are required. In response to vascular injury, platelets are known to adhere to subendothelial surfaces, become activated, and support coagulation. Platelets and other cells may also play an important role in the recruitment of leukocytes into the wound in order to contain microbial invasion.

Endothelium exposed to "rapid" activators such as thrombin and histamine becomes adhesive for neutrophils within two to ten minutes, while endothelium exposed to cytokines such as tumor necrosis factor and interleukin-1 becomes adhesive after one to six hours. The rapid endothelial-dependent leukocyte adhesion has been associated with expression of the lipid mediator platelet activating factor (PAF) on the cell surface, and presumably, the appearance of other endothelial surface receptors. The slower cytokine-inducible endothelial adhesion for leukocytes is mediated, at least in part, by an endothelial cell receptor, ELAM-1, that is synthesized by endothelial cells after exposure to cytokines and then transported to the cell surface, where it binds neutrophils. The isolation, characterization and cloning of ELAM-1 is reviewed by Bevilacqua, et al., in *Science* 243, 1160–1165 (1989). A peripheral lymph node homing receptor, also called "the murine Mel 14 antigen", "Leu 8", the "Leu 8 antigen" and "LAM-1", is another structure on neutrophils, monocytes, and lymphocytes that binds lymphocytes to high endothelial venules in peripheral lymph nodes. The characterization and cloning of this protein is reviewed by Lasky, et al., *Cell* 56, 1045–1055 (1989) (mouse) and Tedder, et al., *J. Exp. Med.*170, 123–133 (1989).

GMP-140 (granule membrane protein 140), also known as PADGEM, is a cysteine-rich and heavily glycosylated integral membrane glycoprotein with an apparent molecular weight of 140,000 as assessed by sodium dodecyl sulfate polyacrylamide gel electrophoresis (SDS-PAGE). GMP-140 was first purified from human platelets by McEver and Martin, *J. Biol. Chem.* 259:9799–9804 (1984). The protein is present in alpha granules of resting platelets but is rapidly redistributed to the plasma membrane following platelet activation, as reported by Stenberg, et al., (1985). The presence of GMP-140 in endothelial cells and its biosynthesis by these cells was reported by McEver, et al., *Blood* 70(5) suppl. 1:355a, Abstract No. 1274 (1987). In endothelial ells, GMP-140 is found in storage granules known as the Weibel-Palade bodies. (McEver, et al. *J. Clin. Invest.* 84:92–99 (1989) and Hattori, et al., *J. Biol. Chem.* 264:7768–7771 (1989)). GMP-140 (called PADGEM) has also been reported to mediate the interaction of activated platelets with neutrophils and monocytes by Larsen, et al., in *Cell* 59, 305–312 (October 1989) and Hamburger and McEver, *Blood* 75:550–554 (1990).

The cDNA-derived amino acid sequence, reported by Johnston, et al., in *Cell* 56, 1033–1044 (Mar. 24 1989), and in U.S. Ser. No. 07/320,408 filed Mar. 8, 1989 now U.S. Pat. No. 8,378,464, indicates that it contains a number of modular domains that are likely to fold independently. Beginning at the N-terminus, these include a "lectin" domain, an "EGF" domain, nine tandem consensus repeats similar to those in complement binding proteins, a transmembrane domain (except in a soluble form that appears to result from differential splicing), and a cytoplasmic tail.

When platelets or endothelial cells are activated by mediators such as thrombin, the membranes of the storage granules fuse with the plasma membrane, the soluble contents of the granules are released to the external environment, and membrane bound GMP-140 is presented within seconds on the cell surface. The rapid redistribution of GMP-140 to the surface of platelets and endothelial cells as a result of activation suggested that this glycoprotein could play an important role at sites of inflammation or vascular disruption.

This important role has been confirmed by the observation that GMP-140 is a receptor for neutrophils (Geng et al., *Nature* 343:757–760 (1990); Hamburger and McEver, *Blood* 75:550–554 (1990)), monocytes (Larsen, et al., *Cell* 59:305–312 (1989); Moore, et al., *J. Cell Biol.* 112:491–499 (1991)), and perhaps a subset of lymphocytes (Moore, et al.,

*J. Cell Biol.* 112:491–499 (1991)). Thus, GMP-140 can serve as a receptor for leukocytes following its rapid mobilization to the surfaces of platelets and endothelial cells stimulated with agonists such as thrombin. This role in leukocyte recruitment may be important in hemostatic and inflammatory processes in both physiologic and pathologic states.

Peptides derived from GMP-140 are described in U.S. Ser. No. 07/554,199 entitled "Functionally Active Selectin-Derived Peptides" filed Jul. 17, 1990 by Rodger P. McEver now abandoned, that are useful in diagnostics and in modulating the hemostatic and inflammatory responses in a patient wherein a therapeutically effective amount of a peptide capable of blocking leukocyte recognition of GMP-140 is administered to the patient. U.S. Ser. No. 07/554,199 filed Jul. 17, 1990 now abandoned, also discloses that peptide sequences within the lectin domain of GMP-140, having homology with the lectin domains of other proteins, especially ELAM-1 and the homing receptor, selectively inhibit neutrophil adhesion to purified GMP-140, and can therefore be used in diagnostic assays of patients and diseases characterized by altered binding by these molecules, in screening assays for compounds altering this binding, and in clinical applications to inhibit or modulate interactions of leukocytes with platelets or endothelial cells involving coagulation and/or inflammatory processes.

ELAM-1, the homing receptor, and GMP-140 have been termed "selectins", based on their related structure and function. ELAM-1 is not present in unstimulated endothelieum. However, when endothelium is exposed to cytokines such as tumor necrosis factor or interleukin-1, the gene for ELAM-1 is transcribed, producing RNA which in turn is translated into protein. The result is that ELAM-1 is expressed on the surface of endothelial cells one to four hours after exposure to cytokines, as reported by Bevilacqua et al., *Proc.Natl.Acad.Sci.USA* 84:9238–9242 (1987) (in contrast to GMP-140, which is stored in granules and presented on the cell surface within seconds after activation). ELAM-1 has been shown to mediate the adherence of neutrophils to cytokine-treated endothelial and thus appears to be important in allowing leukocytes to migrate across cytokine-stimulated endothelium into tissues. The cDNA-derived primary structure of ELAM-1 indicates that it contains a "lectin" domain, an EGF domain, and six (instead of the nine in GMP-140) repeats similar to those of complement-regulatory proteins, a transmembrane domain, and a short cytoplasmic tail. There is extensive sequence homology between GMP-140 and ELAM-1 throughout both proteins, but the similarity is particularly striking in the lectin and EGF domains.

Homing receptors are lymphocyte surface structures that allow lymphocytes to bind to specialized endothelial cells in lymphatic tissues, termed high endothelial cells or high endothelial venules (reviewed by Yednock and Rose, *Advances in Immunology*, vol. 44, F. I. Dixon,ed., 313–378 (Academic Press, New York 1989). This binding allows lymphocytes to migrate across the endothelium into the lymphatic tissues where they are exposed to processed antigens. The lymphocytes then re-enter the blood through the lymphatic system. The homing receptor contains a lectin domain, an EGF domain, two complement-binding repeats, a transmembrane domain, and a short cytoplasmic tail. The homing receptor also shares extensive sequence homology with GMP-140, particularly in the lectin and EGF domains.

Based on a comparison of the lectin domains between GMP-140, ELAM-1, and the homing receptor (LEU-8), it may be possible to select those peptides inhibiting binding of neutrophils to GMP-140 which will inhibit binding of ELAM-1, the homing receptor, and other homologous selecting, to components of the inflammatory process, or, conversely, which will inhibit only GMP-140 binding.

The in vivo significance of platelet-leukocyte interactions has not been studied carefully. However, in response to vascular injury, platelets are known to adhere to subendothelial surfaces, become activated, and support coagulation. Platelets and other cells may also play an important role in the recruitment of leukocytes into the wound in order to contain microbial invasion. Conversely, leukocytes may recruit platelets into tissues at sites of inflammation, as reported by Issekutz, et al., *Lab. Invest.* 49:716 (1983).

The coagulation and inflammatory pathways are regulated in a coordinate fashion in response to tissue damage. For example, in addition to becoming adhesive for leukocytes, activated endothelial cells express tissue factor on the cell surface and decrease their surface expression of thrombomodulin, leading to a net facilitation of coagulation reactions on the cell surface. In some cases, a single receptor can be involved in both inflammatory and coagulation processes.

Proteins involved in the hemostatic and inflammatory pathways are of interest for diagnostic purposes and treatment of human disorders. However, there are many problems using proteins therapeutically. Proteins are usually expensive to produce in quantities sufficient for administration to a patient. Moreover, there can be a reaction against the protein after it has been administered more than once to the patient. It is therefore desirable to develop peptides having the same, or better, activity as the protein, which are inexpensive to synthesize, reproducible and relatively innocuous.

It is preferable to develop peptides which can be prepared synthetically, having activity at least equal to, or greater than, the peptides derived from the protein itself.

It is therefore an object of the present invention to provide peptides interacting with cells recognized by selectins, including GMP-140, ELAM-1, and lymphocyte homing receptor.

It is another object of the present invention to provide methods for using these peptides to inhibit leukocyte adhesion to endothelium or to platelets.

It is a further object of the present invention to provide methods for using these peptides to modulate the immune response and the hemostatic pathway.

It is yet another object of the present invention to provide peptides for use in diagnostic assays relating to GMP-140, ELAM-1, and lymphocyte homing receptor.

SUMMARY OF THE INVENTION

Peptides derived from three regions of the lectin domain of GMP-140 and the related selecting, ELAM-1 and the lymphocyte homing receptor, have been found to inhibit neutrophil adhesion to GMP-140. These and additional peptides have been synthesized having the following formula:

$$R^1\text{-X-A-B-C-D-E-Y-}R^2 \qquad (I)$$

or a pharmaceutically acceptable acid- or based-addition salt thereof wherein:

A is D- or L-asparagine, D- or L-isoleucine or D- or L-valine;

B is D- or L-asparagine or glycine;

C is D- or L-lysine, D- or L-valine or glycine;

D is D- or L-valine, D- or L-threonine or D- or L-isoleucine;

E is D- or L-tryptophan;

X and Y are linear chains of from 0 to 10 amino acids;

$R^1$ is H (signifying a free N-terminal group), formyl, lower alkyl, aryl, lower alkanoyl, aryl, alkyloxycarbonyl or aryloxycarbonyl and $R^2$ is OH (signifying a free C-terminal group) lower alkyl or aryl esters, or $NR^3R^4$ where $R^3$ and $R^4$ each selected independently from H, lower alkyl or aryl.

Peptides of Formula I have as their core region portions of the 56–60 amino acid sequence of GMP-140, with residue 1 defined as the N-terminus of the mature protein after the cleavage of the signal peptide. Examples of peptides of Formula I demonstrate the inhibition of the binding of neutrophils to GMP-140 in concentrations ranging from 5 to 1500 $\mu$M. It has been found that alterations within the core sequence, as well as N-terminal and C-terminal flanking regions, do not result in loss of biological activity.

The peptides are useful as diagnostics and, in combination with a suitable pharmaceutical carrier, for clinical applications in the modulation or inhibition of coagulation processes or inflammatory processes.

DETAILED DESCRIPTION OF THE INVENTION

Figure 1:
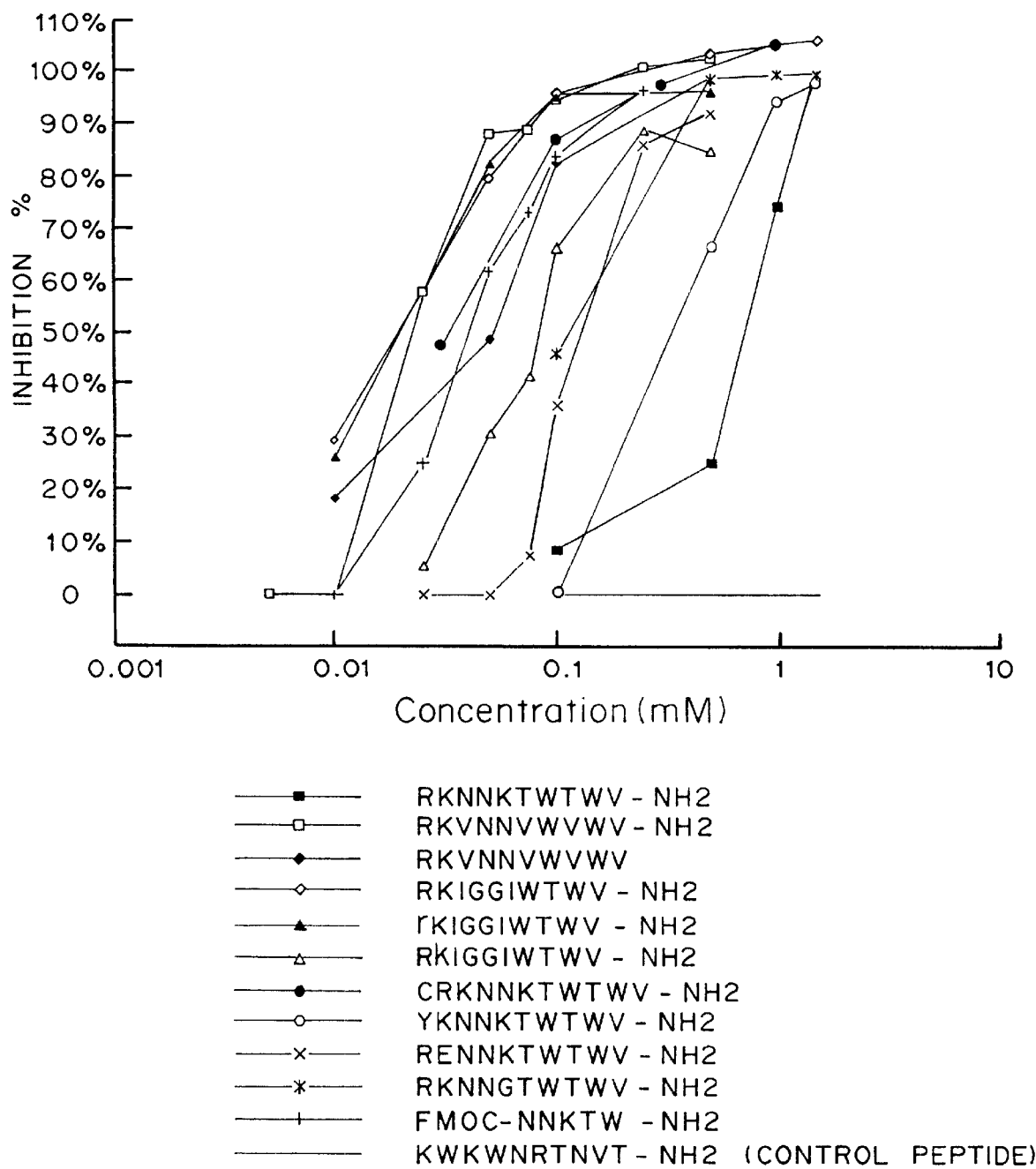
FIG. 1 shows the activity of several peptides of Formula I in inhibiting the binding of neutrophils to GMP-140, % inhibition versus concentration of peptide (mM): RKNNKTWTWV-NH$_2$ (SEQ ID NO:1) (closed squares); RKVNNVWVWV-NH$_2$ (SEQ ID NO:2) (open squares); RKVNNVWVWV (SEQ ID NO:3) (closed diamonds); RKIGGIWTWV-NH$_2$ (SEQ ID NO:4) (open diamonds); rKIGGIWTWV-NH$_2$ (SEQ ID NO:5) (closed triangles); RkIGGIWTWV-NH$_2$ (SEQ ID NO:6) (open triangles); CRKNNKTWTWV-NH$_2$ (SEQ ID NO:7) (closed circles); YKNNKTWTWV-NH$_2$ (SEQ ID NO:8) (open circles); RENNKTWTWV-NH$_2$ (SEQ ID NO:9) (-X-); RKNNGTWTWV-NH$_2$ (SEQ ID NO:10) (->|<-); FMOC-NNKTW-NH$_2$ (SEQ ID NO:11) (-|-); and KWKWNRTNVT-NH$_2$ (--) (SEQ ID NO:12) (control peptide).

Peptides having GMP-140-like activity, therapeutic compositions containing these peptides, methods for the preparation of these peptides, and methods of use thereof are disclosed.

In their broadest scope, the peptides having the following formula:

$$R^1\text{-X-A-B-C-D-E-Y-}R^2 \qquad (I)$$

or a pharmaceutically acceptable sale thereof, wherein:

A is D- or L-asparagine, D- or L-isoleucine or D- or L-valine;

B is D- or L-asparagine or glycine

C is D- or L-lysine, D- or L-valine or glycine;

D is D- or L-valine, D- or L-threonine or D- or L-isoleucine;

E is D- or L-tryptophan;

X and Y are linear chains of from 0 to 10 amino acids;

$R^1$ is H (signifying a free N-terminal group), formyl, lower alkyl, aryl, lower alkanoyl, aroyl, alkyloxycarbonyl or aryloxycarbonyl and $R^2$ is OH (signifying a free C-terminal group) lower alkyl or aryl esters, or $NR^3N^4$ where $R^3$ and $R^4$ each selected independently from H, lower alkyl or aryl.

Preferred peptides are those wherein E is tryptophan, particularly where $R^1$ is H and $R^2$ is $NR^3R^4$.

Most preferred peptides are:

Arg-Lys-Asn-Asn-Lys-Thr-Trp-NH$_2$ (SEQ ID NO:13);

Cys-Ile-Gly-Ile-Arg-Lys-Asn-Asn-Lys-Thr-Trp-Thr-Trp-Val-NH$_2$ (SEQ ID NO:14);

Arg-Lys-Asn-Asn-Lys-Thr-Trp-Thr-Trp-Val-Gly-Thr-Lys-Lys-Ala-Leu-Thr-Asn-Glu-Cys-NH$_2$ (SEQ ID NO:15);

Arg-Lys-Asn-Asn-Lys-Thr-Trp-Thr-Trp-Val-NH$_2$ (SEQ ID NO:1);

Lys-Asn-Asn-Lys-Thr-Trp-NH$_2$ (SEQ ID NO:16);

Acetyl-Asn-Asn-Lys-Thr-Trp-NH$_2$ (SEQ ID NO:17);

Arg-Lys-Asn-Asn-Lys-Thr-Trp-Thr-Trp-Val (SEQ ID NO:18);

Arg-Lys-Val-Asn-Asn-Val-Trp-Val-Trp-Val (SEQ ID NO:3);

Arg-Lys-Val-Asn-Asn-Val-Trp-Val-Trp-Val-NH$_2$ (SEQ ID NO:2);

Arg-Lys-Ile-Gly-Gly-Ile-Trp-Thr-Trp-Val (SEQ ID NO:19);

Arg-Lys-Ile-Gly-Gly-Ile-Trp-Thr-Trp-Val-NH$_2$ (SEQ ID NO:4);

Arg-Lys-Ile-Gly-Gly-Ile-Trp-NH$_2$ (SEQ ID NO:20);

Arg-Lys-Val-Asn-Asn-Val-Trp-NH$_2$ (SEQ ID NO:21);

Ac-Arg-Lys-Asn-Asn-Lys-Thr-Trp-Thr-Trp-Val-NH$_2$ (SEQ ID NO:22);

Cys-Arg-Lys-Asn-Asn-Lys-Thr-Trp-Thr-Trp-Val-NH$_2$ (SEQ ID NO:7);

Arg-Glu-Asn-Asn-Lys-Thr-Trp-Thr-Trp-Val-NH2 (SEQ ID NO:9);

Arg-Lys-Asn-Asn-Lys-Thr-Trp-Thr-Trp-Glu-NH$_2$ (SEQ ID NO:23);

Tyr-Lys-Asn-Asn-Lys-Thr-Trp-Thr-Trp-Val-NH$_2$ (SEQ ID NO:8);

D-Arg-Lys-Ile-Gly-Gly-Ile-Trp-Thr-Trp-Val-NH$_2$ (SEQ ID NO:5);

Arg-D-Lys-Ile-Gly-Gly-Ile-Trp-Thr-Trp-Val-NH$_2$ (SEQ ID NO:6); and

FMOC-Asn-Asn-Lys-Thr-Trp-NH$_2$ (SEQ ID NO:11);

As used herein, the term "lower alkyl" includes branched, straight-chain, and cyclic saturated hydrocarbons having from one to six carbon atoms, such as methyl, ethyl, propyl, isopropyl, butyl, isobutyl, t-butyl, pentyl, isopentyl, neopentyl, cyclopentylmethyl and hexyl. The term "lower alkanoyl" means

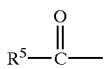

wherein $R^5$ is a lower alkyl group. The term aroyl means

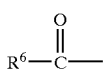

wherein $R^6$ is an aromatic or heteroaromatic structure having between one and three rings, which may or may not be ring fused structures, and are optimally substituted with halogens, carbons, other heteroatoms such as nitrogen (N), sulfur (S), phosphorus (P) and boron (B). The term alkoxycarbonyl means

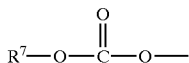

wherein $R^7$ is a lower alkyl group. The term aryloxycarbonyl means

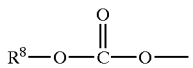

wherein $R^8$ is an aryl or arylmethyl group.

The peptides of formula I can be used in the form of the free peptide or a pharmaceutically acceptable salt. Amine salts can be prepared by treating the peptide with an acid according to known methods. Suitable acids include inorganic acids such as hydrochloric acid, hydrobromic acid, perchloric acid, nitric acid, thiocynaic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, fumaric acid, anthranilic acid, cinnamic acid, naphthalenesulfonic acid, and sulfanilic acid.

Carboxylic acid groups in the peptide can be converted to a salt by treating the peptide with a base according to known methods. Suitable bases include inorganic bases such as sodium hydroxide, ammonium hydroxide, and potassium hydroxide, and organic bases such as mono-, di-, and tri-alkyl and aryl amines (e.g., triethylarnine, diisopropylamine, methylamine, and dimethylarnine and optionally substituted mono-, di, and tri-ethanolamines.

As referred to herein, the amino acid components of the peptides and certain materials used in their preparation are identified by abbreviations for convenience. These abbreviations are as follows:

| | Abbreviations | |
|---|---|---|
| Amino Acid | | |
| L-alanine | Ala | A |
| D-alanine | D-Ala | a |
| L-arginine | Arg | R |
| D-arginine | D-Arg | r |
| D-asparagine | D-Asn | N |
| L-asparagine | L-Asn | n |
| L-aspartic acid | Asp | D |
| D-aspartic acid | D-Asp | d |
| L-cysteine | Cys | C |
| D-cystein | D-Cys | c |
| L-glutamic acid | Glu | E |
| D-glutamic acid | D-Glu | e |
| L-glutamine | Gln | Q |
| D-glutamine | D-Gln | q |
| glycine | Gly | G |
| L-histidine | His | H |
| D-Histidine | D-His | h |
| L-isolelucine | Ile | I |
| D-isoleucine | D-Ile | i |
| L-leucine | Leu | L |
| D-Leucine | D-Leu | l |
| L-Lysine | Lys | K |
| D-Lysine | D-Lys | k |
| L-phenylalanine | Phe | F |
| D-phenylalanine | D-Phe | f |
| L-proline | Pro | P |

-continued

| | Abbreviations | |
|---|---|---|
| D-proline | D-Pro | p |
| L-pyroglutamic acid | pGlu | |
| D-pyroglutamic acid | D-pGlu | |
| L-serine | L-Ser | S |
| D-serine | D-Ser | s |
| L-threonine | L-Thr | T |
| D-threonine | D-Thr | t |
| L-tyrosine | L-Tyr | Y |
| D-tyrosine | D-Tyr | y |
| L-tryptophan | Trp | W |
| D-tryptophan | D-Trp | w |
| L-valine | Val | V |
| D-valine | D-Val | v |
| Reagents | | |
| Trifluoroacetic acid | TFA | |
| Methylene chloride | $CH_2Cl_2$ | |
| N,N-Diisopropylethylamine | DIEA | |
| N-Methylpyrrolidone | NMP | |
| 1-Hydroxybenzotriazole | HOBT | |
| Dimethylsulfoxide | DMSO | |
| Acetic anhydride | $Ac_2O$ | |

Methods of Preparation of Peptides

The peptides can generally be prepared following known techniques, as described for example in the cited publications, the teachings of which are specifically incorporated herein. In a preferred method, the peptides are prepared following the solid-phase synthetic technique initially described by Merrifield in *J.Amer.Chem.Soc.*, 85, 2149–2154 (1963). Other techniques may be found, for example, in M. Bodanszky, et al., *Peptide Synthesis*, second edition (John Wiley & Sons, 1976), as well as in other reference works known to those skilled in the art.

Appropriate protective groups usable in such syntheses and their abbreviations will be found in the above text, as well as in J. F. W. McOmie, *Protective Groups in organic Chemistry*, (Plenum Press, New York, 1973). The common protective groups used herein are t-butyloxycarbonyl (Boc), fluorenylmethoxycarbonyl (FMOC), benzyl (Bzl), tosyl (Tos), o-bromo-phenylmethoxycarbonyl (BrCBZ), phenylmethoxycarbonyl (CBZ), 2-chloro-phenylmethoxycarbonyl (2-Cl-CBZ), 4-methoxy-2,3,6-trimethylbenzenesulfonyl (Mtr), trityl (Trt), formyl (CHO), and tertiary butyl (t-Bu). General synthetic procedures for the synthesis of peptides of Formula I by solid phase methodology are as follows:

| | | REPETITIONS | TIME |
|---|---|---|---|
| A. General Synthetic procedures for Solid Phase Synthesis using $N^\alpha$-Boc Protection. | | | |
| 1. | 25% TFA in $CH_2Cl_2$ | 1 | 3 min |
| 2. | 50% TFA in $CH_2Cl_2$ | 1 | 16 min |
| 3. | $Ch_2Cl_2$ | 5 | 3 min |
| 4. | 5% DIEA in NMP | 2 | 4 min |
| 5. | NMP | 6 | 5 min |
| 6. | Coupling step | 1 | 57 min |
| a. | Preformed BOC-Amino Acid-HOBT active ester in NMP | | 36 min |
| b. | DMSO | | 16 min |
| c. | DIEA | | 5 min |
| 7. | 10% $Ac_2O$, 5% DIEA in NMP | 1 | 9 min |
| 8. | $CH_2Cl_2$ | 5 | 3 min |
| B. General Synthetic Procedure For Solid Phase Peptide Synthesis Using | | | |

-continued

|   | | REPETITIONS | TIME |
|---|---|---|---|
| | $N^\alpha$-FMOC Protection | | |
| 1. | 20% piperdine in NMP | 1 | 3 min |
| 2. | 20% piperdine in NMP | 1 | 15 min |
| 3. | NMP | 6 | 9 min |
| 4. | Coupling Preformed FMOC-Amino Acid-HOBT active ester in NMP | 1 | 71 min |
| 5. | NMP | 6 | 7 min |

N-terminal acetylation on the deprotected $N^\alpha$-amino group of peptides synthesized using either Boc or FMOC strategies is accomplished with 10% $Ac_2O$ and 5% DIEA in NMP, followed by washing of the peptide resin with NMP and/or $CH_2Cl_2$.

The peptides can also be prepared using standard genetic engineering techniques known to those skilled in the art. For example, the peptide can be produced enzyrnaticaly by inserting nucleic acid encoding the peptide into an expression vector, expressing the DNA, and translating the DNA into the peptide in the presence of the required amino acids. The peptide is then purified using chromatographic or electrophoretic techniques, or by means of a carrier protein which can be fused to, and subsequently cleaved from, the peptide by inserting into the expression vector in phase with the peptide encoding sequence a nucleic acid sequence encoding the carrier protein. The fusion protein-peptide may be isolated using chromatographic, electrophoretic or immunological techniques (such as binding to a resin via an antibody to the carrier protein). The peptide can be cleaved using chemical methodology or enzymatically, as by, for example, hydrolases.

Methods of Preparation of Pharmaceutical Compositions

To prepare the pharmaceutical compositions containing these peptides, a peptide of Formula I or a base or acid addition salt thereof is combined as the active ingredient with a pharmaceutical carrier according to conventional pharmaceutical compounding techniques. This carrier may take a wide variety of forms depending on the form of preparation desired for administration, e.g., sublingual, rectal, nasal, oral, or parenteral. In preparing the compositions in oral dosage form, any of the usual pharmaceutical media may be employed, for example, water, oil, alcohols, flavoring agents, preservatives, and coloring agents, to make an oral liquid preparation (e.g., suspension, elixir, or solution) or with carriers such as starches, sugars, diluents, granulating agents, lubricants, binders, and disintegrating agents, to make an oral solid preparation (e.g., powder, capsule, or tablet).

Controlled release forms or enhancers to increase bioavailability may also be used. Because of their ease in administration, tablets and capsules represent the most advantageous oral dosage unit form, in which case solid pharmaceutical carriers are employed. If desired, tablets may be sugar coated or enteric coated by standard techniques.

For parenteral products, the carrier will usually be sterile water, although other ingredients to aid solubility or as preservatives may be included. Injectable suspensions may also be prepared, in which case appropriate liquid carriers and suspending agents can be employed.

The peptides can also be administered locally at a wound or inflammatory site by topical application of a solution or cream.

Alternatively, the peptide may be administered in liposomes or microspheres (or microparticles). Methods for preparing liposomes and microspheres for administration to a patient are known to those skilled in the art. U.S. Pat. No. 4,789,734 describe methods for encapsulating biological materials in liposomes. Essentially, the material is dissolved in an aqueous solution, the appropriate phospholipids and lipids added, along with surfactants if required, and the material dialyzed or sonicated, as necessary. A review of known methods is by G. Gregoriadis, Chapter 14. "Liposomes", *Drug Carriers in Biology and Medicine* pp. 287–341 (Academic Press, 1979). Microspheres formed of polymers or proteins are well known to those skilled in the art, and can be tailored for passage through the gastrointestinal tract directly into the bloodstream. Alternatively, the peptide can be incorporated and the microspheres, or composite of microspheres, implanted for slow release over a period of time, ranging from days to months. See, for example, U.S. Pat. Nos. 4,906,474, 4,925,673, and 3,625,214.

The peptides are generally active when administered parenterally in amounts above about 1 $\mu$g/kg body weight. For treatment to prevent organ injury in cases involving reperfusion, the peptides may be administered parenterally from about 0.01 to about 10 mg/kg body weight. Generally, the same range of dosage amounts may be used in treatment of the other diseases or conditions where inflammation is to be reduced.

Methods for Demonstrating Binding

Peptides that are biologically active are those which inhibit binding of neutrophils, monocytes, subsets of lymphnocytes or other cells to GMP-140, or which inhibit leukocyte adhesion to endothelium that is mediated by ELAM-1 and/or the homing receptor.

Peptides can be screened for their ability to inhibit adhesion to cells, for example, neutrophil adhesion to purified GMP-140 immobilized on plastic wells, using the assay described by Geng, et al., *Nature* 343, 757–760 (1990).

Human neutrophils are isolated from heparinized whole blood by density gradient centrifugation on Mono-Poly resolving media, Flow laboratories. Neutrophil suspensions are greater than 98% pure and greater than 95% viable by trypan blue exclusion. For adhesion assays, neutrophils are suspended at a concentration of $2\times10^6$ cells/mL in Hanks' balanced salt solution containing 1.26 mM $Ca^{2+}$ and 0.81 mM $Mg^{2+}$ (HBSS, Gibco) with 5 mg/mL human serum albumin (HBSS/HSA). Adhesion assays are conducted in triplicate in 96-well microtiter plates, Corning, incubated at 4° C. overnight with 50 microliters of various protein solutions.

GMP-140 is isolated from human platelet lysates by immunoaffinity chromatography on antibody S12-Sepharose™ and ion-exchange chromatography on a Mono-Q™ column (FLPC, Pharmacia Fine Chemicals, as follows.

Outdated human platelet packs (100 units) obtained from a blood bank and stored at 4° C. are pooled, adjusted to 5 mM EDTA at pH 7.5, centrifuged at 4,000 rpm for 30 min in 1 liter bottles, then washed three times with 1 liter of 0.1 M NaCl, 20 mM Tris pH 7.5 (TBS), 5 mM EDTA, 5 mM benzamidine.

The pellets are then resuspended in a minimum amount of wash buffer and made 1 mM in DIFP, then frozen in 50 mL screwtop tubes at −80° C. The frozen platelets are thawed and resuspended in 50 mL TBS, 5 mM benzamidine, 5 mM EDTA pH 7.5, 100 M leupeptin. The suspension is frozen and thawed two times in a dry ice-acetone bath using a 600 mL lyophilizing flask, then homogenized in a glass/teflon mortar and pestle and made 1 mM in DIFP. The NaCl concentration is adjusted to 0.5 M with a stock solution of 4 M NaCl. After stirring the suspension at 4° C., it is centrifuged in polycarbonate tubes at 33,000 rpm for 60 min at 4° C. The supernatant (0.5 M NaCl wash) is removed and saved; this supernatant contains the soluble form of GMP-140. Care is taken not to remove the top part of the pellet with the supernatant. The pellets are then homogenized in extraction buffer (TBS, 5 mM benzamidine, 5 mM EDTA, pH 7.5, 100 $\mu$M leupeptin, 2% Triton X-100). After centrifugation at 19,500 rpm for 25 min at 4° C., the supernatant is removed. The extraction procedure is repeated with the pellet and the supernatant is combined with the first supernatant. The combined extracts, which contain the membrane form of GMP-140, are adjusted to 0.5 M NaCl.

The soluble fraction (0.5 M NaCl wash) and the membrane extract (also adjusted to 0.5 M NaCl) are absorbed with separate pools of the monoclonal antibody S12 (directed to human GMP-140) previously coupled to Affigel (Biorad) at 5 mg/mL for 2 h at 4° C. After letting the resins settle, the supernatants are removed. The S12 Affigel containing bound GMP-140 is then loaded into a column and washed overnight at 4° C. with 400 mL of 0.5 M NaCl, 20 mM Tris pH 7.5, 0.01% Lubrol PX.

Bound GMP-140 is eluted from the S12 Affigel with 100 mL of 80% ethylene glycol, 1 mM MES pH 6.0, 0.01% Lubrol PX. Peak fractions with absorbance at 280 nm are pooled. Eluates are dialyzed against TBS with 0.05% Lubrol, then applied to a Mono Q column (FPLC from Pharmacia). The concentrated protein is step eluted with 2 M NaCl, 20 mM Tris pH 7.5 (plus 0.05% Lubrol PX for the membrane fraction). Peak fractions are dialyzed into TBS pH 7.5 (plus 0.05% Lubro PX for the membrane fraction).

GMP-140 is plated at 5 micrograms/mL and the control proteins: human serum albumin (Alb), platelet glycoprotein Iib/IIIha (Iib), von Willebrand factor (vWF), fibrinogen (FIB), thrombomodulin™, gelatin (GEL) or human serum (HS), are added at 50 micrograms/mL. All wells are blocked for 2 h at 22° C. with 300 microliters HBSS containing 10 mg/mL HSA, then ashed three times with HBSS containing 0.1% Tween-20 and once with HBSS. Cells ($2\times10^5$ per well are added to the wells and incubated at 22° C. for 20 min. The wells are then filled with HGSS/HSA, sealed with acetate tape (Dynatech), and centrifuged inverted at 150 g for 5 min. After discarding nonadherent cells and supernates, the contents of each well are solubilized with 200 microliters of 0.5% hexadecyltrimethylammonium bromide, Sigma, in 50 mM potassium phosphate, pH 6.0, and assayed for myeloperoxidase activity, Ley, et al., *Blood* 73, 1324–1330 (1989). The number of cells bound is derived from a standard curve of myeloperoxidase activity versus numbers of cells. Under all assay conditions, the cells release less than 5% of total myeloperoxidase and lactate dehydrogenase. Inhibition is read as a lower percent adhesion, so that a value of 5% means that 95% of the specific adhesion was inhibited.

Clinical Applications

The peptides are generally active when administered parenterally in amounts above about 1 $\mu$g/kg body weight. For treatment to prevent organ injury in cases involving reperfusion, the peptides may be administered parenterally from about 0.01 to about 10 mg/kg body weight. Generally, the same range of dosage amounts may be used in treatment of the other diseases or conditions where inflammation is to be reduced. This dosage will be dependent, in part, on whether one or more peptides are administered. A synergistic effect may be seen with combinations of peptides from different, or overlapping, regions of the lectin domain, or in combination with peptides derived from the EGF domain of GMP-140.

Since the selectins have several functions related to leukocyte adherence, inflammation, and coagulation, clinically, compounds which interfere with binding of GMP-140, ELAM-1 or LEU-8 can be used to modulate these responses.

For example, the peptides can be used to competitively inhibit leukocyte adherence by competitively binding to GMP-140 receptors on the surface of leukocytes. This kind of therapy would be particularly useful in acute situations where effective, but transient, inhibition of leukocyte-mediated inflammation is desirable. Chronic therapy by infusion of the peptides may also be feasible in some circumstances.

An inflammatory response may cause damage to the host if unchecked, because leukocytes release many toxic molecules that can damage normal tissues. These molecules include proteolytic enzymes and free radicals. Examples of pathological situations in which leukocytes can cause tissue damage include injury from ischemia and reperfusion, bacterial sepsis and disseminated intravascular coagulation, adult respiratory distress syndrome, tumor metastasis, rheumatoid arthritis and atherosclerosis.

Reperfusion injury is a major problem in clinical cardiology. Therapeutic agents that reduce leukocyte adherence in ischemic myocardium can significantly enhance the therapeutic efficacy of thrombolytic agents. Thrombolytic therapy with agents such as tissue plasinogen activator or streptokinase can relieve coronary artery obstruction in many patients with severe myocardial eschemia prior o irreversible myocardial cell death. However, many such patients still suffer myocardial neurosis despite restoration of blood flow. This "reperfusion injury" is known to be associated with adherence of leukocytes to vascular endothelium in the ischemic zone, presumably in part because of activation of platelets and endothelium by thrombin and cytokines that makes them adhesive for leukocytes (Romson et al., *Circulation* 67: 1016–1023, 1983). These adherent leukocytes can migrate through the endothelium and destroy ischemic myocardium just as it is being rescued by restoration of blood flow.

There are a number of other common clinical disorders in which ischemia and reperfusion results in organ injury mediated by adherence of leukocytes to vascular surfaces, including strokes; mesenteric and peripheral vascular disease; organ transplantation; and circulatory shock (in this case many organs might be damaged following restoration of blood flow).

Bacterial sepsis and disseminated intravascular coagulation often exist concurrently in critically ill patients. They are associated with generation of thrombin, cytokines, and other inflammatory mediators, activation of platelets and endothelium, and adherence of leukocytes and aggregation of platelets throughout the vascular system. Leukocyte-dependent organ damage is an important feature of these conditions.

Adult respiratory distress syndrome is a devastating pulmonary disorder occurring in patients with sepsis or following trauma, which is associated with widespread adherence and aggregation of leukocytes in the pulmonary circulation. This leads to extravasation of large amounts of plasma into the lungs and destruction of lung tissue, both mediated in large part by leukocyte products.

Two related pulmonary disorders that are often fatal are in immunosuppressed patients undergoing allogeneic bone marrow transplantation and in cancer patients suffering from complications that arise from generalized vascular leakage resulting from treatment with interleukin-2 treated LAK cells (Lymphokine-activated lymphocytes). LAK cells are known to adhere to vascular walls and release products that are presumably toxic to endothelium. Although the mechanism by which LAK cells adhere to endothelium is not known, such cells could potentially release molecules that activate endothelium and then bind to endothelium by mechanisms similar to those operative in neutrophils.

Tumor cells from many malignancies (including carcinomas, lymphomas, and sarcomas) can metastasize to distant sites through the vasculature. The mechanisms for adhesion of tumor cells to endothelium and their subsequent migration are not well understood, but may be similar to those of leukocytes in at least some cases. The association of platelets with metastasizing tumor cells has been well described, suggesting a role for platelets in the spread of some cancers.

Platelet-leukocyte interactions are believed to be important in atherosclerosis. Platelets might have a role in recruitment of monocytes into atherosclerotic plaques; the accumulation of monocytes is known to be one of the earliest detectable events during atherogenesis. Rupture of a fully developed plaque may not only lead to platelet deposition and activation and the promotion of thrombus formation, but also the early recruitment of neutrophils to an area of ischemia.

Another area of potential application is in the treatment of rheumatoid arthritis.

The criteria for assessing response to therapeutic modalities employing these peptides are dictated by the specific condition and will generally follow standard medical practices. For example, the criteria for the effective dosage to prevent extension of myocardial infarction would be determined by one skilled in the art by looking at marker enzymes of myocardial necrosis in the plasma, by monitoring the electrocardiogram, vital signs, and clinical response. For treatment of acute respiratory distress syndrome, one would examine improvements in arterial oxygen, resolution of pulmonary infiltrates, and clinical improvement as measured by lessened dyspnea and tachypnea. For treatment of patients in shock (low blood pressure), the effective dosage would be based on the clinical response and specific measurements of function of vital organs such as the liver and kidney following restoration of blood pressure. neurologic function would be monitored in patients with stroke. Specific tests are used to monitor the functioning of transplanted organs; for example, serum creatinine, urine flow, and serum electrolytes in patients undergoing kidney transplantation.

Diagnostic Reagents.

The peptides can also be used for the detection of human disorders in which the ligands for the selectins might be defective. Such disorders would most likely be seen in patients with increased susceptibility to infections in which leukocytes might not be able to bind to activated platelets or endothelium. Cells to be tested, usually leukocytes, are collected by standard medically approved techniques and screened. Detection systems include ELISA procedures, binding of radiolabeled antibody to immobilized activated cells, flow cytometry, or other methods known to those skilled in the arts. Inhibition of binding in the presence and absence of the lectin domain peptides can be used to detect defects or alterations in selectin binding. For selecting, such disorders would most likely be seen in patients with increased susceptibility to infections in which leukocytes would have defective binding to platelets and endothelium because of deficient leukocyte ligands for GMP-140. The peptide is labeled radioactively, with a fluorescent tag, enzymatically, or with electron dense material such as gold for electron microscopy. The cells to be examined, usually leukocytes, are incubated with the labeled peptides and binding assessed by methods described above with antibodies to GMP-140, or by other methods known to those skilled in the art. If ligand for GMP-140 are also found in the plasma, they can also be measured with standard ELISA or radioimmunoassay procedures, using labeled BMP-140-derived peptide instead of antibody as the detecting reagent.

The following examples are presented to illustrate the invention without intending to specifically limit the invention thereto. In the examples and throughout the specifications, parts are by weight unless otherwise indicated.

EXAMPLE 1

Preparation of Arginyl-lysyl-asparaginyl-asparaginyl-lysyl-threonyl-tryptophyl-threonyl-tryptophyl-valine-amide (SEQ ID NO:1)

The peptide was prepared on an ABI model 431A peptide synthesizer using Version 1.12 of the standard scale Boc software. The amino acids used were Boc-(Tos)Arg, Boc-(ClZ)Lys, Box-Asn, Boc-(Bzl)Thr, Boc-(CHO)Trp, and Boc-Val. 4-methylbenzhydrylamine resin (0.625 g, 0.5 mmol) was used in the synthesis. The final weight of the peptide resin was 1.63 g. The peptide was cleaved from the resin (1.49 g) using 15 mL of HF and 1.5 mL of anisole for 60 min at 0° C. The hydrogen fluoride was evaporated using a stream of nitrogen, the resulting mixture triturated with ether, and the ether removed by filtration. The resulting solids were extracted with cold 0.1 M piperidine (5×10 mL). The extracts were combined and stirred for three hours at 0° C. 1 mL of acetic acid was added. The resultant slurry was lyophilized to yield 0.83 g of crude peptide. The crude peptide was purified byHPLC (multiple injections) on a Vydac C-18 (10μ, 2.2×25 cm) column eluted with a gradient of 15–30% acetonitrile in 0.1% TFA over 30 min at a flow rate of 3 mL per min. Fractions were collected analyzed by HPLC and pure fractions pooled and lyophilized to yield 35 mg of pure peptide. Amino acid analysis: Arg 0.96 (1.0); Asx 1.95 (2.0); Lys 2.16 (2.0); Thr 1.76 (2.0); Trp 1.45 (2.); Val 0.98 (1.0). FAB/MS:MH$^+$ 1332.

EXAMPLE 2

Preparation of Arginyl-lysyl-valyl-asparaginyl-asparaginyl-valyl-tryptophyl-valyl-tryptophyl-valine-amide (SEQ ID NO:2)

The peptide was prepared on an ABI model 431A peptides synthesizer using Version 1.12 of the standard scale Boc software. The amino acids used were Boc-(Tos)Arg, Boc-(ClZ)Lys, Boc-Val, Boc-Asn, and Boc-(CHO)Trp. 4-methylbenzhydrylamine resin (0.625 g, 0.5 mmol) was used in the synthesis. The resin peptide was treated with 1

M ethanolamine in DMF with 5% water (2×30 min) to deformylate the tryptophan. After washing and drying the final weight of the resin was 1.3 g. The peptide was cleaved from the resin (1.25 g) using 15 mL of HF and 0.75 g p-cresol and 0.75 g p-thiocresol for 60 minutes at 0° C. The hydrogen fluoride was removed using a stream of dry nitrogen, the residue triturated with ether and the ether removed by filtration. The remaining solids were triturated with a 50% solution of TFA in methylene chloride. The resin was removed by filtration, the solution evaporated under reduced pressure and the residue triturated with ether to give 0.79 g of the crude peptide, isolated by filtration. The crude peptide (0.3 g) was purified by HPLC (multiple injections) on a Vydac C-18 column (10μ, 2.2×25 cm) eluting with a gradient of 10–30% acetonitrile in 0.1% aqueous TFA over 180 minutes at a flow rate of 3 mL/min. Fractions were collected, analyzed by HPLC and pure fractions pooled and lyophilized to give 21 mg of pure peptide. Amino acid analysis: Asx 2.01 (2.0); Val 4.07 (4.0); Lys 0.96 (1.0); Trp 1.93 (2.0); Arg 1.02 (1.0). FAB/MS: MH$^+$ 1299.

EXAMPLE 3

Preparation of Arginyl-lysyl-asparaginyl-asparaginyl-lysyl-threonyl-tryptophyl-threonyl-tryptophyl-valyl-glycyl-threonyl-lysyl-lysyl-alanyl-leucyl-cysteine-amide (SEQ ID NO:24)

The peptide was prepared on ABI model 431A peptide synthesizer using Version 1.12 of the standard scale Boc software. The amino acids used in the synthesis were Boc-(Tos)Arg, Boc-(ClZ)Lys, Boc-Asn, Boc-(Bzl)Thr, Boc-(CHO)Trp, Boc-Val, Boc-Gly, Boc-Ala, Boc-Leu, and Boc-(4-Me-Bzl) Cys. 4-methylbenzhydrylamine resin (0.625 g, 0.5 mmol) was used in the synthesis. Final weight of the peptide resin was 1.85 g. The tryptophan residues on the resin peptide were deformylated using a solution of 1 M ethanolamine in dimethylformamide with 5% water (2×30 min). The resin was washed with DMF, ethanol and dried to a constant weight of 1.85 g. The peptide was cleaved from the resin (1.75 g) with 15 mL of HF, 1 mL of p-cresol, and 1 mL of p-thiocresole for 60 minutes at 0° C. The HF was removed by a nitrogen stream. The resulting solids were triturated with ether, collected by filtration and washed with ether. The peptide was extracted from the resin with 50% TFA in methylene chloride (5×20 mL). Precipitation with ether gave 0.96 g of crude peptide. The crude peptide (0.40 g) was purified on a Vydac C-18 column (15μ, 5×25 cm) eluting with a 20 to 30% gradient of acetonitrile in 0.1% aqueous TFA over 120 minutes at a flow rate of 15 mL per minute. Fractions were collected, analyzed by HPLC and pure fractions pooled and lyophilized to give 42 mg of the peptide. A second purification was done by HPLC on a Vydac C-18 column (10μ, 2.2×25 cm) using a 10–20% gradient of acetonitrile in 0.1% TFA over 120 min at a flow rate of 3 mL per min. Fractions were collected, analyzed by HPLC and pure fractions pooled and lyophilized to give 10 mg of the pure peptide. Amino acid analysis: Asx 2.04 (2.0), Thr 2.84 (3.0), Gly 1.03 (1.0), Ala 0.97 (1.0), Cys N.D. (1.0), Val 1.00 (1.0), Leu 1.02 (1.0), Lys 4.04 (4.0), Trp N.D. (20), Arg 0.05 (1.0). FAB/MS: MH$^+$ 2035.

EXAMPLE 4

Preparation of Arginyl-lysyl-isoleucyl-glycyl-glycyl-isoleucyl-tryptophyl-threonyl-tryptophyl-valine-amide (SEQ ID NO:4)

The peptide was prepared by manual solid phase synthesis using Boc chemistry. The amino acids used were Boc-(Tos) Arg, Boc-(ClZ)Lys, Boc-Ile, Boc-Gly, Boc-(Bzl)Thr, Boc-(CHO)Thr, Boc-(CHO)Trp, and Boc-Val. 4-Methylbenzhydrylamine resin (6.25 g, 5.0 mmol) was used in synthesis. The final weight of the peptide resin was 1.35 g. The peptide was cleaved from the resin (1.21 g) using 16 mL of HF, 1.2 mL anisole and 0.4 mL thiophenol for one hour at 0° C. The HF was removed by a nitrogen stream. The residue was triturated with ether and the ether removed by filtration. The remaining solids were extracted with 25 mL of a 50% solution of TFA in methylene chloride. Removal of the resin by filtration, evaporation of solution and trituration of the residue gave 0.52 g of crude peptide. The tryptophan was deformylated with 100 mL 0.1 M aqueous piperidine for one hour at 0° C. The reaction mixture was evaporated and the residue dissolved in water and lyophilized. The crude peptide (0.31 g) was purified by HPLC (multiple injections) on a Vydac C-18 column (10μ, 2.2×25 cm) eluting with a gradient of 25% to 75% acetonitrile in 0.1% TFA over 100 minutes at a flow rate of 3 mL/min. Fractions were collected, analyzed by HPLC and pure fractions pooled and lyophilized to give 28 mg of pure peptide. Amino Acid Analysis: Arg 1.02 (1.0), Gly 2.06 (2.0), Ile 1.92 (2.0), Lys 1.00 (1.0), Thr 0.95 (1.0), Trp 1.42 (2.0), Val 0.98 (1.0). FAB/MS: MH$^+$=1214.

EXAMPLE 5

Preparation of Arginyl-lysyl-valyl-asparaginyl-asparaginyl-valyl-tryptophyl-valyl-tryptophyl-valine (SEQ ID NO:3)

The peptide was prepared on an ABI Model 431A peptide synthesizer using Version 1.12 of the standard scale FMOC software. The amino acids used for the synthesis were FMOC-(Mtr)Arg FMOC-(Boc)Lys, FMOC-Val, FMOC-Asn, and FMOC-Trp. Wang resin (0.245 g, 0.25 mmol) was used in the synthesis. The final weight of the resin was 0.53 g. The peptide was cleaved from the resin using 6 mL of a mixture of 10 mL TFA, 0.7 g phenol, 0.75 mL ethanedithiol, 0.5 mL anisole and 0.5 mL water at ambient temperature for 1.5 hrs. The resin was removed by filtration and the peptide precipitated from the filtrate by the addition of ether. The crude peptide (0.18 g) was purified by HPLC (2×90 mg) on a Vydac C-18 column (10μ, 2.2×25 cm) eluting with a 20–50% gradient of acetonitrile in 0.1% TFA over 120 min at a rate of 15 mL/min. Fractions containing pure peptide were pooled and lyophilized to yield 30 mg of pure product. Amino acid analysis: Asx 2.14 (2.0), Val 3.80 (4.0), Lys 0.95 (1.0), Trp 1.02 (2.0), Arg 1.03 (1.0). FAB:MS MH$^+$ 1299.

EXAMPLE 6

Preparation of Cysteinyl-isoleucyl-glycyl-isoleucyl-arginyl-lysyl-asparaginyl-asparaginyl-lysyl-threonyl-tryptophyl-threonyl-tryptophyl-valine-amide (SEQ ID NO:14)

The peptide was prepared on an ABI Model 431A peptide synthesizer using Version 1.12 of the standard scale FMOC software. The amino acids used for the synthesis were Boc-(4-Me-Bzl)Cys, Boc-Ile, Boc-Gly, Boc-(Tos)Arg, Boc (ClZ)Lys, Boc-Asn, Boc-(Bzl)Thr, Boc-(CHO)Trp and Boc-Val. 4-methylbenzhydrylamine resin (0.632 g, 0.5 mmol) was used in the synthesis. The final weight of the resin was 1.83 g. The typtophans on the peptide resin were deformylated using 1 M ethanolamine in a mixture of 95% DMF and 5% water. The peptide resin was isolated by filtration and dried under reduced pressure. The peptide was cleaved from the resin (1.31 g) using 20 mL of HF, 1.4 mL anisole, and 0.6 mL thiophenol for 60 min at 0° C. The HF removed using a stream of dry nitrogen. The residue was triturated with ether and the ether removed by filtration. The remaining solids wee extracted with 25 mL of a 50% solution of TFA in methylene chloride. Removal of the resin by filtration, evaporation under reduced pressure and trituration of the residue gave 0.55 g of crude peptide. The crude peptide (0.32 g) was purified by HPLC (multiple injections) on a Vydac C-18 column, (10μ, 2.2×25 cm) eluting with a gradient of 17.5% to 37.5% acetonitrile in 0.1% TFA over 90 minutes at a flow rate of 6 mL/min. Fractions were collected, analyzed by HPLC and pure fractions pooled and lyophilized to give 20 mg of pure peptide. Amino Acid Analysis: Arg 0.91 (1.0), Asx 2.08 (2.0), Cys 0.96 (1.0), Gly 1.00 (1.0), Ile 1.70 (2.0), Lys 2.00 (2.0), Thr 1.83 (0), Trp 1.19 (20), Val 1.05 (1.0). FAB/MS: MH+ 1717.

EXAMPLE 7

Preparation of Arginyl-lysyl-asparaginyl-asparaginyl-lysyl-threonyl-tryptophyl-threonyl-tryptophyl-valyl-glycyl-threonyl-lysyl-lysyl-alanyl-leucyl-threonyl-asparaginyl-glutamyl-cysteine-amide (SEQ ID NO:15)

The peptide was prepared on an ABI model 431A peptides synthesizer using Version 1.12 of the standard scale Boc software. The amino acids used were Boc-(Tos)Arg, Boc-(ClZ)Lys, Box-Asn, Box-(Bzl)Thr, Boc-CHO)Trp, Boc-Val, Boc-Gly, Boc-Ala, Boc-Leu, Boc-(Bzl)Glu, and Boc-(ACM)Cys. 4-methylbenzhydrylamine resin (0.625 g, 0.5 mmol) was used in the synthesis. The tryptophan residues on the peptide resin were deformylated using 1 M ethanolamine in a mixture of 95% DMF and 5% water (2×20 mL×30 min). The final weight of the resin peptide was 2.13 g. The peptide was cleaved from the resin (2.06 g) using 2 mL of p-cresol, 0.8 g dithiothreitol and 20 mL HF for one hour at 0° C. The hydrogen fluoride was removed by a stream of dry nitrogen followed by aspiration. The residue was triturated with ether, the resulting solids removed by filtration and the peptide extracted from the resin (5×10 mL) with 10% acetic acid. The extracts were passed through a G-15 gel filtration column (2.5×29 cm) eluting with 1% acetic acid. Appropriate fractions were combined and lyophilized to give 0.44 g of crude peptide.

Analysis showed deformylation of the tryptophan residues to be incomplete, therefore, 0.39 g of the crude peptide was treated with 10 mL of 0.1 M aqueous piperidine for 1 hr at 0° C. The pH was adjusted to between 4 and 5 with 70% acetic acid and the crude peptide solution purified by HPLC using Vydac C-18 column (10μ, 2.2×25 cm), eluting with a gradient of 0 to 37.5% acetonitrile in 0.1% TFA over 42 minutes at a flow rate of 10 mL per minute. Fractions were collected and the fractions containing the pure peptide pooled and lyophilized to yield 19 mg of a yellowish solid. This material was dissolved in 1.2 mL of 30% acetic acid and treated with 8 mg of mercury (II) acetate for 1 hr at ambient temperature to remove the Acm protecting group. After one hour, 12 mg of dithiothreitol was added and stirring continued for an additional hour. The resulting precipitate was removed by filtration and the filtrate loaded onto a G-15 column (2.5×29 cm) and eluted with 30% acetic acid. Appropriate fractions were pooled and lyophilized to give 17 mg of the pur peptide as an off-white solid. Amino acid analysis: Ala 0.99 (1.0), Arg 0.86 (1.0), Asx 2.89 (3.0), Glx 1.06 (1.0), Gly 1.08 (1.0), Leu 1.08 (1.0), Lys 3.87 (4.0), Thr 3.68 (4.0), Trp N.D. (2.0), Val 1.17 (1.0). FAB/MS: MH+ 2377.

EXAMPLE 8

Preparation of Arginyl-lysyl-asparaginyl-asparaginyl-lysyl-threonyl-tryptophyl-hreonyl-tryptophyl-valine (SEQ ID NO:18)

The peptide was prepared on an ABI Model 4131A peptide synthesizer using Version 1.12 of the standard Boc software. The amino acids used were Boc-(Tos)Arg, Boc-(ClZ)Lys, Boc-Asn, Boc-(Bzl)Thr, and Boc-(CHO)Trp. Boc-Valyl-PAM resin (0.83 g, 0.5 mmol) was used in the synthesis. The final weight of the resin peptide was 1.34 g. The peptide was cleaved from the resin (1.0 g) using 10 mL of HF and 1.0 mL of anisole for 60 min at 0° C. The hydrogen fluoride was removed using a stream of nitrogen and the residue triturated with ether. Solids were removed by filtration, the peptide extracted from the resin using 1 M acetic acid, and the extract lyophilized to yield 0.32 g of crude peptide. The formyl groups from the tryptophan residues were removed using 0.1 M piperidine in a 1:1 mixture of DMF/water for two hours at ambient temperatures. The crude peptide (0.15 g) was purified by HPLC (3×50 mg) using a Vydac C-18 column (10μ, 2.2×25 cm) eluting with a 25–50% gradient of 50% acetonitrile in 0.1% TFA over 120 minutes at a flow rate of 15 mL per minute. Fractions were collected, analyzed by HPLC and pure fractions pooled and lyophilized to give 48 mg of the desired product. Amino acid analysis: Arg 0.99 (1.0), Asx 2.01 (2.0), Lys 1.97 (2.0), Thr 1.85 (2.0), Trp 1.93 (2.0), Val 1.02 (1.0).

EXAMPLE 9

Preparation of Arginyl-lysyl-asparaginyl-asparaginyl-lysyl-threonyl-tryptophyl-threonyl-tryptophan-amide (SEQ ID NO:25)

The peptide was prepared on an ABI Model 431A peptide synthesizer using Version 1.12 of the standard Boc software. The amino acids used were Boc-(Tos)Arg, Boc-(ClZ)Lys, Boc-Asn, Boc-(Bzl)Thr, and Boc(CHO)Trp. 4-Methylbenzhydrylamine resin (0.625 g, 0.5 mmol) was used in the synthesis. The final weight of the resin was 1.44 g. The peptide was cleaved from the resin (1.0 g) using 10 mL of HF and 1.1 mL of anisole for 60 min at 0° C. The hydrogen fluoride was evaporated using a stream of nitrogen and the resulting mixture triturated with ether. Solids were removed by filtration and extracted with 1 M acetic acid to yield 0.38 mg of crude peptide. The formyl groups on the tryptophan residues were removed using 0.1 M piperidine in 50% aqueous DMF for two hours at ambient temperature. The crude peptide (0.2 g) was purified by HPLC (2×0.1 g) on a Vydac C-18 column (15μ, 5×25 cm) eluting with a 25–50% gradient of acetonitrile in 1% TFA over 120 minutes at a flow rate of 15 mL per minute. Fractions were collected, analyzed by HPLC and pure fractions pooled and lyophilized to give 48 mg of pure peptide. Amino acid analysis: Arg 1.00 (1.0), Asx 2.01 (2.0), Lys 1.99 (2.0), Thr 1.87 (2.0), Trp 2.04 (2.0).

EXAMPLE 10

Preparation of Arginyl-lysyl-asparaginyl-asparaginyl-glycyl-threonyl-tryptophyl-threonyl-tryptophyl-valine-amide (SEQ ID NO:10)

The peptide was prepared on an ABI Model 431A peptide synthesizer using Version 1.12 of the standard scale Boc software. The amino acids used were Boc-(Tos)Arg, Boc-(Clz)Lys, Boc-Asn, Boc-Gly Boc-(Bzl)Thr, Boc-(CHO)Trp and Boc-Val. 4-Methylbenzhydrylamine resin (0.625 g, 0.5 mmol.) was used in the synthesis. The final weight of the resin was 1.19 g. The peptide was cleaved from the resin (1.0 g) using 10 mL of hydrogen fluoride and 1 mL of anisole for 60 minutes at 0° C. The hydrogen fluoride was evaporated using a stream of nitrogen and the resulting mixture triturated with ether. The solids were removed by filtration and extracted with 1 M acetic acid to give 0.41 g of crude peptide after lyophilization. The formyl groups were removed from the tryptophan using a 0.1 M solution of piperidine in 50% aqueous DMF for two hours at ambient temperature. The crude peptide (0.12 g) was purified by HPLC (multiple injections) on a Vydac C-18 column (15 u5, 5×25 cm) eluting with a 25–50% gradient of acetonitrile in 0.1% TFA over 120 minutes at a flow rate of 15 mL per minute. Fractions were collected, analyzed by HPLC and pure fractions pooled and lyophilized to give 40 mg of pure product. Amino acid analysis: Arg 0.98 (1.0), Asx 1.98 (2.0), Gly 1.04 (1.0), Lys 0.98 (1.0), Thr 1.82 (2.0), Trp 1.95 (2.0), Val 1.01 (1.0).

EXAMPLE 11

Inhibition of Neutrophil Binding to GMP140 Coated Wells

Binding of various peptides to GMP-140 coated wells, as described above, were compared. The results are shown in FIG. 1.

Binding of the peptides at various concentrations, ranging from 0.05 to 1 mM were compared. The peptides tested and the percent inhibition of neutrophil binding to GMP-140 is shown in Table I.

The testing was conducted as follows:

A 5 µg/mL solution of GMP-140 in HBSS (buffer) is prepared. 50 µL is pipetted per well with the exception of three wells (A10 to A12) and the plate is stored overnight at 0° C. to 4° C. The liquids are removed by aspiration and 300 µL of 5 mg/mL human serum albumin (HSA)/HBSS is placed in the wells coated with GMP-140 plus the three non-coated wells to be used as control wells. The plate is allowed to incubate at room temperature for two hours. The HSA/HBSS solution is removed and the wells washed three times with 300 µL/well of HBSS. The third 300 µL wash of HBSS is left in each well and the plate is kept at room temperature until it is used.

Eight to ten mL of fresh human blood collected in heparinized tubes is carefully layered over 5 mL of the Mono-Poly Resolving Medium in 15 mL polypropylene centrifuge tubes. The tubes are centrifuged for 30 minutes at room temperature and 1400 to 1600 rpm. The tubes are rotated 180° and centrifuged for another 30 minutes under the same conditions. The top plasma layer and first cellular layer of leukocytes are drawn off. The second cellular layer of neutrophils is harvested (usually 2 to 3 mL per tube) and is placed in a clean 15 mL centrifuge tube. This is then underlayered with 1.5 mL of fresh resolving medium and spun at 2000 rpm for 15 minutes at room temperature. This is done to further purify the neutrophils from residual red blood cells. The neutrophils in the supernatant are collected, placed in a clean 15 mL centrifuge tube and HSA/HBSS is added to bring the volume to 15 mL. The tube is gently inverted 3 or 4 times and is centrifuged at 1400 rpm for 5 minutes to pellet the neutrophils. The supernatant is removed by aspiration and the cells resuspended gently in HSA/HBSS (2 to 5 mL, depending on pellet size) and the cells/Ml determined using a hemacytometer and microscope. The cells are diluted to $2 \times 10^6$ cells/mL with HSA/HBSS.

A 3 mM concentration of the peptide to be tested expressed in mg/mL is calculated as follows:

molecular weight/percent peptide×0.003.

Peptides are accurately weighed into clean 4 mL flint glass vials with screw caps. The amount weighed should be enough to produce 0.5 to 1 mL of the 3 mM stock based on the mg/mL value calculated above. The peptides are dissolved in an amount of 25 mM HEPES buffered HBSS that is calculated as follows:

(peptide weighed out)/(mg/mL for 3 mM solution)=mL of buffer.

The peptides are incubated with the neutrophils at 1.0, 0.3, 0.1 and 0.03 mM concentrations for 30 to 35 minutes at room temperature in 1.5 mL flip top polypropylene centrifuge tubes as follows:

| Amount of 3 mM stock | Amount of 25 mM HEPES/HBSS | Amount of Neutrophil suspension |
| --- | --- | --- |
| 1.00 mM | 200 µL | 0 | 400 µL |
| 0.30 mM | 60 µL | 140 µL | 400 µL |
| 0.10 mM | 20 µL | 180 µL | 400 µL |
| 0.03 mM | 6 mM | 194 µL | 400 µL |

800 µL of neutrophil suspension is mixed with 400 µL of the 25 mM HEPES buffered HBSS pH 7.4 and the whole is incubated for 30 to 35 minutes at room temperature.

150 µL of the neutrophil suspension/25 mM HEPES buffered HBSS pH 7.4 is pipetted into designated GMP-140 coated and HSA wells. 150 µL of the appropriate peptide/neutrophil suspension incubate is pipetted onto designated GMP-140 coated wells. All are incubated on the plate for 20 minutes at room temperature. The liquids are removed by mild aspiration and the wells are washed twice with HSA/HBSS and are checked to make sure no liquid remains after the final aspiration. 200 µL of the 0.5% HTAB buffer is added to each well. After incubating at room temperature for 20 minutes, an eight channel multi-pipetter fitted with the appropriate tips is set for 100 µL is used to agitate the contents of the wells four times.

The contents of each well is tested in a clean Nunc 96 well flat-bottomed polystyrene microtitration plate. The reagents are added as follows:

1) 15 µL of ample (0.5% HTAB buffer from plate well)
2) 55 µL of 80 mM potassium phosphate buffer pH 5.4
3) 20 µl OF 3.0 Mm $H_2O_2$ in the 80 mM potassium phosphate buffer pH 5.4
4) 10 ugL of 16 mM 3,3',5,5'-tetramethylbenzidine in 50% dimethylformamide/80 mM potassium phosphate buffer.

The plate is developed for 5 to 15 minutes at room temperature and the reaction is stopped by the addition of 100 µL of 1 M phosphoric acid. The plate is read in the single filter mode with the filter set at 450 nm. Blanking is set against air.

The calculations are performed by the BioCalc 1.06 software. The mean and standard deviation for each test peptide concentration, neutrophil controls (neutrophils on HSA blocked wells only) and neutrophil standards (neutrophils on GMP-140 coated HSA blocked wells) are obtained via standard formulas in the software. The coefficient of variation for each sample, standard or control is calculated by formulas I created in the BioCalc software of the format:

C.V.=(standard deviation/mean)×100

The % inhibition for each sample is calculated as follows:

$$\% \text{ inhibition} = 1 - \frac{(\text{sample mean} - \text{control mean})}{(\text{standard mean} - \text{control mean})}$$

The results demonstrate that, with the exception of the negative control, the peptides all inhibit neutrophil binding to immobilized GMP-140.

Modifications and variations of the present invention, synthetic peptides and methods for modulating binding reactions involving selectins, will be obvious to those skilled in the art from the foregoing detailed description. Such modifications and variations are intended to come within the scope of the appended claims.

TABLE I

PERCENT INHIBITION OF NEUTROPHIL BINDING TO GMP-140 BY SYNTHETIC PEPTIDES.

| STRUCTURE | CONCENTRATION (mM) | | |
|---|---|---|---|
| | 0.1 | 0.5 | 1.0 |
| RKVNNVW-NH$_2$ (SEQ ID NO:21) | | | 17% |
| RKVNNVWVWV (SEQ ID NO:3) | 82% | 98% | |
| RKVNNVWVWV-NH$_2$ (SEQ ID NO:2) | 94% | 102% | |
| CRKNNKTWTWV-NH$_2$ (SEQ ID NO:7) | 87% | | 105% |
| RKNNKTW-NH$_2$ (SEQ ID NO:13) | 31% | 53% | 99% |
| RKNNKTWT-NH$_2$ (SEQ ID NO:26) | 26% | 23% | 34% |
| RKNNKTWTWV (SEQ ID NO:18) | 14% | | 35% |
| Ac-RKNNKTWTWV-NH$_2$ | 35% | 50% | |

TABLE I-continued

PERCENT INHIBITION OF NEUTROPHIL BINDING TO GMP-140 BY SYNTHETIC PEPTIDES.

| STRUCTURE | CONCENTRATION (mM) | | |
|---|---|---|---|
| | 0.1 | 0.5 | 1.0 |
| (SEQ ID NO:22) RENNKTWTWV-NH$_2$ | 34% | 94% | 96% |
| (SEQ ID NO:9) RKNNKTWTWE-NH$_2$ | 17% | 20% | |
| (SEQ ID NO:23) RKNNGTWTWV-NH$_2$ | 46% | 99% | 99% |
| (SEQ ID NO:10) RKNNKTWTWV-NH$_2$ | 13% | 20% | 33% |
| (SEQ ID NO:1) YKNNKTWTWV-NH$_2$ | 9% | 98% | 104% |
| (SEQ ID NO:8) RKNNKTWTWVGTKKALTNEC-NH$_2$ | 9% | | 47% |
| (SEQ ID NO:15) FMOC-NNKTW-NH$_2$ | 85% | 100% | 99% |
| (SEQ ID NO:11) rKIGGIWTWV-NH$_2$ | 95% | 96% | |
| (SEQ ID NO:5) RkIGGIWTWV-NH$_2$ | 67% | 88% | 97% |
| (SEQ ID NO:6) RKIGGIWTWV-NH$_2$ | 96% | 103% | 105% |
| (SEQ ID NO:4) RKNNKTWTWV-NH$_2$ | 14% | 30% | 87% |
| (SEQ ID NO:1) KWKWNRTNVT-NH$_2$ (control peptide) | 0% | 0% | 0% |
| (SEQ ID NO:12) | | | |

---

We claim:

1. A peptide inhibiting binding of selectins selected from the group having the formula:

$$R^1\text{-}X\text{-}A\text{-}B\text{-}C\text{-}D\text{-}E\text{-}Y\text{-}R^2$$

or a pharmaceutically acceptable acid- or base-addition salt thereof wherein:

A is D- or L-asparagine, D- or L-isoleucine or D- or L-valine;

B is D- or L-asparagine or glycine;

C is D- or L-lysine, D- or L-valine or glycine;

D is D- or L-valine, D- or L-threonine or D- or L-isoleucine;

E is D- or L-tryptophan;

X and Y are linear chains of from 0 to 10 amino acids;

$R^1$ is H, formyl, lower alkyl, aryl, lower alkanoyl, aroyl, alkyloxycarbonyl or aryloxycarbonyl and $R^2$ is OH, lower alkyl or aryl esters, or $NR^3R^4$ where $R^3$ and $R^4$ are each selected independently from H, lower alkyl or aryl; and wherein the peptide does not include a peptide comprising L amino acids wherein X is arginine-lysine, C is lysine or glycine, and Y is threonine-tryptophan-valine or valine-tryptophan-valine.

2. The peptide of claim 1 wherein X is selected from the group consisting of Arg-Lys, Ile-Arg-Lys, Gly-Ile-Arg-Lys (SEQ ID NO:27), Ile-Gly-Ile-Arg-Lys (SEQ ID NO:28), Ac-Arg-Lys, Cys-Arg-Lys, Arg-Glu, Tyr-Lys, D-Arg-Lys, Arg-D-Lys, and Cys-Ile-Gly-Ile-Arg-Lys (SEQ ID NO:29).

3. A peptide inhibiting binding of selectins selected from the group having the formula:

$$R^1\text{-}X\text{-}A\text{-}B\text{-}C\text{-}D\text{-}E\text{-}Y\text{-}R^2$$

or a pharmaceutically acceptable acid- or base-addition salt thereof wherein:

A is D- or L-asparagine, D- or L-isoleucine or D- or L-valine;

B is D- or L-asparagine or glycine;

C is D- or L-lysine, D- or L-valine or glycine;

D is D- or L-valine, D- or L-threonine or D- or L-isoleucine;

E is D- or -tryptophan;

X is a linear chain from 0 to 10 amino acids;

$R^1$ is H, formyl, lower alkyl aryl, lower alkanoyl, aroyl, alkyloxycarbonyl or aryloxycarbonyl and $R^2$ is OH, lower alkyl or aryl esters, or $NR^3R^4$ where $R^3$ and $R^4$ are each selected independently from H, lower alkyl or aryl; and wherein the peptide does not include a peptide comprising L amino acids wherein X is arginine-lysine and C is lysine or glycine;

and wherein Y is selected from the group consisting of Thr, Val, Thr-Trp, Thr-Trp-Val, Val-Trp, Val-Trp-Val, Thr-Trp-Val-Gly-Thr-Lys (SEQ ID NO:30), Thr-Trp-Val-Gly-Thr-Asn (SEQ ID NO:31), Thr-Trp-Val-Gly-Thr-Gln (SEQ ID NO:32), Val-Trp-Val-Gly-Thr-Gln (SEQ ID NO:33), Val-Trp-Val-Gly-Thr-Lys (SEQ ID NO:34), Val-Trp-Val-Gly-Thr-Asn (SEQ ID NO:35), Thr-Trp-Glu, and Thr-Trp-Val-Gly-Thr-Lys-Lys-Ala-Leu-Thr-Asn-Glu-Cys (SEQ ID NO:36).

4. A peptide inhibiting binding of selectins selected from the group consisting of peptides having the formula:

Arg-Lys-Asn-Asn-Lys-Thr-Trp-NH$_2$ (SEQ ID NO:13);

Lys-Asn-Asn-Lys-Thr-Trp-NH$_2$ (SEQ ID NO:16);

Acetyl-Asn-Asn-Lys-Thr-Trp-NH$_2$ (SEQ ID NO:17);

Arg-Lys-Ile-Gly-Gly-Ile-Trp-NH$_2$ (SEQ ID NO:20);

Arg-Lys-Val-Asn-Asn-Val-Trp-NH$_2$ (SEQ ID NO:21);

Arg-Glu-Asn-Asn-Lys-Thr-Trp-Thr-Trp-Val-NH$_2$ (SEQ ID NO:9);

Arg-Lys-Asn-Asn-Lys-Thr-Trp-Thr-Trp-Glu-NH$_2$ (SEQ ID NO:23);

Tyr-Lys-Asn-Asn-Lys-Thr-Trp-Thr-Trp-Val-NH$_2$ (SEQ ID NO:8);

D-Arg-Lys-Ile-Gly-Gly-Ile-Trp-Thr-Trp-Val-NH$_2$ (SEQ ID NO:5);

Arg-D-Lys-Ile-Gly-Gly-Ile-Trp-Thr-Trp-Val-NH$_2$ (SEQ ID NO:6);

FMOC-Asn-Asn-Lys-Thr-Trp-NH$_2$ (SEQ ID NO:11) and pharmaceutically acceptable acid- or base-addition salts thereof.

5. The peptide of claim 1 in combination with a pharmaceutical carrier selected from the group consisting of carriers suitable for parenteral administration, oral administration, topical administration, and controlled release formulations.

6. A method for inhibiting binding of a selectin in a patient in need of treatment thereof comprising administering to the patient in a pharmaceutically acceptable carrier a peptide having the formula:

$$R^1\text{-}X\text{-}A\text{-}B\text{-}C\text{-}D\text{-}E\text{-}Y\text{-}R^2$$

or a pharmaceutically acceptable acid- or base-addition salt thereof wherein:

A is D- or L-asparagine, D- or L-isoleucine or D- or L-valine;

B is D- or L-asparagine or glycine;

C is D- or L-lysine, D- or L-valine or glycine;

D is D- or L-valine, D- or L-threonine or D- or L-isoleucine;

E is D- or L-tryptophan;

X and Y are linear chains of from 0 to 10 amino acids;

$R^1$ is H, formyl, lower alkyl, aryl, lower alkanoyl, aroyl, alkyloxycarbonyl or aryloxycarbonyl and $R^2$ is OH, lower alkyl or aryl esters, or $NR^3R^4$ where $R^3$ and $R^4$ are each selected independently from H, lower alkyl or aryl, wherein the peptide is provided in an amount effective to inhibit binding of the selectin; and wherein the peptide does not include a peptide comprising L amino acids wherein X is arginine-lysine, C is lysine or glycine, and Y is threonine-tryptophan-valine or valine-tryptophan-valine.

7. The method of claim 6 wherein X is selected from the group consisting of Arg-Lys, Ile-Arg-Lys, Gly-Ile-Arg-Lys (SEQ ID NO:27), Ile-Gly-Ile-Arg-Lys (SEQ ID NO:28), Ac-Arg-Lys, Cys-Arg-Lys, Arg-Glu, Tyr-Lys, D-Arg-Lys, Arg-D-Lys, and Cys-Ile-Gly-Ile-Arg-Lys (SEQ ID NO:29).

8. A method for inhibiting binding of a selectin in a patient in need of treatment thereof comprising administering to the patient in a pharmaceutically acceptable carrier an effective amount to inhibit selectin binding of a peptide having the formula:

$$R^1\text{-}X\text{-}A\text{-}B\text{-}C\text{-}D\text{-}E\text{-}Y\text{-}R^2$$

or a pharmaceutically acceptable acid- or base-addition salt thereof wherein:

A is D- or L-asparagine, D- or L-isoleucine or D- or L-valine;

B is D- or L-asparagine or glycine;

C is D- or L-lysine, D- or L-valine or glycine;

D is D- or L-valine, D- or L-threonine or D- or L-isoleucine;

E is D- or L-tryptophan;

X is a linear chain of from 0 to 10 amino acids;

$R^1$ is H, formyl, lower alkyl, aryl, lower alkanoyl, aroyl, alkyloxycarbonyl or aryloxycarbonyl and $R^2$ is OH, lower alkyl or aryl esters, or $NR^3R^4$ where $R^3$ and $R^4$ are each selected independently from H, lower alkyl or aryl; and wherein the peptide does not include a peptide comprising L amino acids wherein X is arginine-lysine and C is lysine or glycine;

and wherein Y is selected from the group consisting of Thr, Val, Thr-Trp, Thr-Trp-Val, Val-Trp, Val-Trp-Val, Thr-Trp-Val-Gly-Thr-Lys (SEQ ID NO:30), Thr-Trp-Val-Gly-Thr-Asn (SEQ ID NO:3 1), Thr-Trp-Val-Gly-Thr-Gln (SEQ ID NO:32), Val-Trp-Val-Gly-Thr-Gln (SEQ ID NO:33), Val-Trp-Val-Gly-Thr-Lys (SEQ ID NO:34), Val-Trp-Val-Gly-Thr-Asn (SEQ ID NO:35), Thr-Trp-Glu, and Thr-Trp-Val-Gly-Thr-Lys-Lys-Ala-Leu-Thr-Asn-Glu-Cys (SEQ ID NO:36).

9. A method for inhibiting binding of a selectin in a patient in need of treatment thereof comprising administering to the patient in a pharmaceutically acceptable carrier an effective amount to inhibit selectin binding of a peptide wherein the peptide is selected from the group consisting of peptides having the formula:

Arg-Lys-Asn-Asn-Lys-Thr-Trp-$NH_2$ (SEQ ID NO:13);

Lys-Asn-Asn-Lys-Thr-Trp-$NH_2$ (SEQ ID NO:16);

Acetyl-Asn-Asn-Lys-Thr-Trp-$NH_2$ (SEQ ID NO:17);

Arg-Lys-Ile-Gly-Gly-Ile-Trp-$NH_2$ (SEQ ID NO:20);

Arg-Lys-Val-Asn-Asn-Val-Trp-$NH_2$ (SEQ ID NO:21);

Arg-Glu-Asn-Asn-Lys-Thr-Trp-Thr-Trp-Val-$NH_2$ (SEQ ID NO:9);

Arg-Lys-Asn-Asn-Lys-Thr-Trp-Thr-Trp-Glu-$NH_2$ (SEQ ID NO:23);

Tyr-Lys-Asn-Asn-Lys-Thr-Trp-Thr-Trp-Val-$NH_2$ (SEQ ID NO:8);

D-Arg-Lys-Ile-Gly-Gly-Ile-Trp-Thr-Trp-Val-$NH_2$ (SEQ ID NO:5);

Arg-D-Lys-Ile-Gly-Gly-Ile-Trp-Thr-Trp-Val-$NH_2$ (SEQ ID NO:6);

FMOC-Asn-Asn-Lys-Thr-Trp-$NH_2$ (SEQ ID NO:11); and pharmaceutically acceptable acid- or base-addition salts thereof.

10. The method of claim 6 wherein the pharmaceutical carrier is selected from the group consisting of carriers suitable for parenteral administration, oral administration, topical administration, and controlled release formulations.

* * * * *